(12) United States Patent
Kruecker et al.

(10) Patent No.: US 12,402,863 B2
(45) Date of Patent: Sep. 2, 2025

(54) ULTRASOUND IMAGE-BASED IDENTIFICATION OF ANATOMICAL SCAN WINDOW, PROBE ORIENTATION, AND/OR PATIENT POSITION

(71) Applicant: KONINKLIJKE PHILIPS N.V., Eindhoven (NL)

(72) Inventors: Jochen Kruecker, Andover, MA (US); Gary Cheng-How Ng, Redmond, WA (US); Raghavendra Srinivasa Naidu, Auburndale, MA (US); Man M Nguyen, Melrose, MA (US); Hua Xie, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 69 days.

(21) Appl. No.: 18/267,592

(22) PCT Filed: Dec. 13, 2021

(86) PCT No.: PCT/EP2021/085353
§ 371 (c)(1),
(2) Date: Jun. 15, 2023

(87) PCT Pub. No.: WO2022/128838
PCT Pub. Date: Jun. 23, 2022

(65) Prior Publication Data
US 2024/0074738 A1 Mar. 7, 2024

Related U.S. Application Data

(60) Provisional application No. 63/127,429, filed on Dec. 18, 2020.

(51) Int. Cl.
*A61B 8/00* (2006.01)
*G06T 7/00* (2017.01)
(Continued)

(52) U.S. Cl.
CPC .............. *A61B 8/54* (2013.01); *A61B 8/4254* (2013.01); *A61B 8/463* (2013.01); *A61B 8/469* (2013.01);
(Continued)

(58) Field of Classification Search
CPC ......... A61B 8/54; A61B 8/463; A61B 8/4477; A61B 8/4245; G16H 30/40;
(Continued)

(56) References Cited

U.S. PATENT DOCUMENTS 6,315,724 B1 * 11/2001 Berman .............. G01S 15/8993
600/443
7,117,026 B2   10/2006 Grewer et al.
(Continued)

FOREIGN PATENT DOCUMENTS

EP     3463099 A1    4/2019
EP     3847967 A1    7/2021
(Continued)

OTHER PUBLICATIONS

International Search Report and Written Opinion for PCT/EP2021/085353; Mailing date: Apr. 4, 2022, 10 pages.

*Primary Examiner* — Oommen Jacob

(57) ABSTRACT

An ultrasound imaging system includes an a processor circuit that stores, in a memory in communication with the processor circuit, a target parameter representative of a target anatomical scan window. The processor circuit receives a first ultrasound image acquired by a first ultrasound probe with a first anatomical scan window during a first acquisition period. The processor circuit determines a first parameter representative of the first anatomical scan window. The processor circuit retrieves the target parameter from the memory. The processor circuit compares the target parameter and the first parameter. The processor circuit
(Continued)

outputs a visual representation of the comparison to a display in communication with the processor circuit.

2 Claims, 17 Drawing Sheets

(51) Int. Cl.
*G06T 7/73* (2017.01)
*G16H 30/40* (2018.01)

(52) U.S. Cl.
CPC .............. *G06T 7/0014* (2013.01); *G06T 7/74* (2017.01); *G16H 30/40* (2018.01); *G06T 2207/10132* (2013.01); *G06T 2207/20084* (2013.01); *G06T 2207/20092* (2013.01); *G06T 2207/30004* (2013.01); *G06T 2207/30196* (2013.01)

(58) Field of Classification Search
CPC .......... G06T 2207/10132; G06T 2207/20092; G06T 7/0014; G06T 7/74
See application file for complete search history.

(56) References Cited

U.S. PATENT DOCUMENTS

| | | |
|---|---|---|
| 7,794,398 B2 | 9/2010 | Salgo |
| 8,144,950 B2 | 3/2012 | Peters et al. |
| 8,698,795 B2 | 4/2014 | Grewer et al. |
| 10,290,076 B2 | 5/2019 | Kadoury et al. |
| 10,424,044 B2 | 9/2019 | Radulescu et al. |
| 10,709,425 B2 | 7/2020 | Waechter-Stehle et al. |
| 2009/0264760 A1 | 10/2009 | Lazebnik et al. |
| 2010/0113887 A1* | 5/2010 | Kalafut .................. A61B 8/481 600/300 |
| 2012/0238875 A1* | 9/2012 | Savitsky .............. G09B 23/286 600/443 |
| 2013/0184584 A1* | 7/2013 | Berkey ................ A61B 8/5292 600/441 |
| 2017/0340310 A1 | 11/2017 | Carlini et al. |
| 2019/0008480 A1 | 1/2019 | Gerard et al. |
| 2019/0012432 A1* | 1/2019 | Sokulin ................. G06T 7/0012 |
| 2019/0125298 A1* | 5/2019 | Abolmaesumi ...... A61B 8/4405 |
| 2019/0142392 A1 | 5/2019 | Carolus et al. |
| 2024/0074738 A1* | 3/2024 | Kruecker ................ G16H 30/40 |

FOREIGN PATENT DOCUMENTS

| | | |
|---|---|---|
| WO | 2005099579 A1 | 10/2005 |
| WO | 2021099171 A1 | 5/2021 |

* cited by examiner

ULTRASOUND IMAGE-BASED IDENTIFICATION OF ANATOMICAL SCAN WINDOW, PROBE ORIENTATION, AND/OR PATIENT POSITION

CROSS-REFERENCE TO PRIOR APPLICATIONS

This application is the U.S. National Phase application under 35 U.S.C. § 371 of International Application No. PCT/EP2021/085353, filed on Dec. 13, 2021, which claims the benefit of U.S. Provisional Patent Application No. 63/127,429, filed on Dec. 18, 2020. These applications are hereby incorporated by reference herein.

TECHNICAL FIELD

The present disclosure relates generally to ultrasound imaging. For example, an ultrasound system can estimate the anatomical scan window, ultrasound probe orientation, and/or patient position for one ultrasound image, compare these parameters to those of another ultrasound image, and provide corresponding guidance so that, e.g., the parameters for the images match.

BACKGROUND

A medical ultrasound system may include an ultrasound transducer probe coupled to a processing system and one or more display devices. Ultrasound imaging systems are widely used for medical imaging and measurement. For example, ultrasound imaging systems may be used to make measurements of organs, lesions, tumors, or other structures within a patient's anatomy. A physician may want to conduct a longitudinal study of any of these structures. The longitudinal study may require the patient to be imaged multiple times over a long period of time. In this way, the physician can track changes to the structure of the patient's anatomy over time.

Ultrasound imaging systems are generally underused in longitudinal studies because reproducible ultrasound image acquisition is challenging. In particular, reliably reproducing two-dimensional (2D) ultrasound imaging is challenging due to the manual nature of image acquisition that includes variations in positioning for both the ultrasound probe and the patient. These variations make it difficult to know if changes in anatomy in a longitudinal study are due to changes in the patient's body or changes due to ultrasound imaging. These variations are also typically not recorded from one ultrasound imaging procedure to the next because they are not easily captured. In addition, physiological parameters such as heart rate, respiratory rate, and tissue morphology can make identification of previously used imaging conditions difficult. For contrast-enhanced ultrasound (CEUS), an imaging technique involving injection of a contrast agent, the timing between injection and imaging presents an additional challenge. All of these factors lead to increased variability in ultrasound-based measurements, in particular for images obtained at different time points. It is also difficult to determine if differences between images or measurements are caused by physiological changes within the patient anatomy or differences in the image acquisition technique. Despite its challenges, however, ultrasound imaging remains a less expensive and safer imaging method than imaging modalities more commonly used in longitudinal studies.

SUMMARY

Embodiments of the present disclosure are systems, devices, and methods for automatically identifying an anatomical scan window, ultrasound probe orientation, and/or patient position associated with an ultrasound image using a deep learning network. By identifying and recording one or more of these parameters for each ultrasound image acquired during a longitudinal study, they may be retrieved at subsequent imaging procedures and used to assist a sonographer, physician, and/or other user in obtaining an additional ultrasound image with the same parameters. This advantageously reduces variability in image acquisition and ultrasound measurements between imaging procedures and may help to make ultrasound imaging a more viable, cost-effective, and safe option for longitudinal studies.

At one imaging procedure, an ultrasound imaging system may acquire an image. A deep learning network may then receive the image as an input. The network may also receive inertial measurement unit (IMU) data from the ultrasound probe as an additional input. The network may identify the anatomical scan window and/or probe orientation used to acquire the ultrasound image based on characteristics of the image itself. The network may also use IMU data to determine the position of the patient at the time the image was acquired. These parameters may then be stored with the ultrasound image.

At a subsequent imaging procedure, the ultrasound imaging system may retrieve the same ultrasound image from the previous procedure along with the anatomical scan window, probe orientation, and/or patient position for the image. The ultrasound system outputs the retrieved scan window, probe orientation, patient position, and/or the earlier image to, e.g., a display to provide guidance for the user (e.g., sonographer or physician). The user can then use this guidance to position the patient and ultrasound probe during the subsequent imaging procedure. Again, the deep learning network may receive this new image and determine the scan window, probe orientation, and/or patient position of the new image. These new parameters may be compared with the parameters from the previous procedure. The ultrasound system may then notify if the parameters match or differ. If the parameters differ, the sonographer may be prompted to adjust the patient or probe positions and acquire an additional image. This process may continue until all the parameters match. The user can record the images in the new procedure when the parameters match. In this manner, the longitudinal study can be more accurately completed, with variations due to probe or patient positioning minimized or eliminated. Rather, the changes in the ultrasound images from the different imaging sessions are due to changes in the patient's body (e.g., progression of disease, effect of treatment, etc.).

In an exemplary aspect, an ultrasound imaging system comprises: a processor circuit configured to: store, in a memory in communication with the processor circuit, a target parameter representative of a target anatomical scan window; receive a first ultrasound image acquired by a first ultrasound probe with a first anatomical scan window during a first acquisition period; determine a first parameter representative of the first anatomical scan window; retrieve the target parameter from the memory; compare the target parameter and the first parameter; and output a visual representation of the comparison to a display in communication with the processor circuit.

In some aspects, the target parameter comprises an anatomical scan window of a second ultrasound probe for a second ultrasound image acquired during a second acquisition period before the first acquisition period. In some aspects, the processor circuit is configured to: store the second ultrasound image in the memory such that the target parameter is associated with the second ultrasound image in the memory. In some aspects, the processor circuit is configured to: receive the second ultrasound image obtained by the second ultrasound probe; determine the target parameter representative of the second anatomical scan window; and associate the target parameter and the second ultrasound image. In some aspects, the processor circuit is configured to: associate the first parameter and the first ultrasound image; store the first parameter and the first ultrasound image in the memory such that the first parameter and the first ultrasound image are associated in the memory; and retrieve the first parameter from the memory for comparison with a further parameter corresponding to a further ultrasound image. In some aspects, the processor circuit is configured for communication with the first ultrasound probe, and wherein the processor circuit is configured to: control the first ultrasound probe to acquire the first ultrasound image; and output, to the display, a screen display comprising at least one of the second ultrasound image or the target parameter, during acquisition of the first ultrasound image. In some aspects, the processor circuit is configured to output, to the display, a screen display comprising the target parameter, the first parameter, the first ultrasound image, the second ultrasound image, and the visual representation of the comparison displayed simultaneously. In some aspects, the first parameter is representative of a first orientation of the first ultrasound probe during the first acquisition period, and wherein the target parameter is representative of a second orientation of the second ultrasound probe during the second acquisition period.

In some aspects, the system further comprises the first ultrasound probe, and the first ultrasound probe comprises an inertial measurement unit, wherein the processor circuit is configured to determine the first parameter based on data obtained by the inertial measurement unit. In some aspects, the first parameter comprises a continuous variable, and wherein the processor circuit is configured to output a visual representation of the continuous variable to the display. In some aspects, the first parameter is representative of a patient position during the first acquisition period. In some aspects, the processor circuit is configured to: receive a user input selecting a target anatomical scan window; and determine the target parameter based on the user input. In some aspects, the processor circuit comprises a preprocessor and at least one deep learning network. In some aspects, the preprocessor is configured to: receive a plurality of ultrasound images acquired by the first ultrasound probe during the first acquisition period, wherein the plurality of ultrasound images comprises the first ultrasound image; buffer the plurality of ultrasound images in the memory; filter the plurality of ultrasound images; and output a subset of the plurality of ultrasound images to the deep learning network. In some aspects, the preprocessor, to filter the plurality of ultrasound images, is configured to: determine a similarity metric for the plurality of ultrasound images buffered in the memory; and remove a portion of the plurality of ultrasound images from the memory based on the similarity metric to yield the subset of the plurality of ultrasound images. In some aspects, the at least one deep learning network comprises a plurality of deep learning networks respectively corresponding to a plurality of organs, and the preprocessor is configured to: identify an organ in the first ultrasound image; and output the first ultrasound image to a deep learning network corresponding to the organ. In some aspects, the at least one deep learning network comprises a single deep learning network corresponding to a plurality of organs. In some aspects, the deep learning network is configured to determine the first parameter. In some aspects, the deep learning network comprises a convolutional neural network (CNN). In some aspects, the CNN is trained using a dataset of ultrasound images associated with corresponding training parameters determined based on information from a tracking system. In some aspects, the visual representation of the comparison comprises: a first indicator when the target parameter and the first parameter are the same; and a second indicator when the target parameter and the first parameter are different. In some aspects, the processor circuit is configured to: store, in the memory, a second patient physiological condition during the second acquisition period; receive a first patient physiological condition during the first acquisition period; retrieve the second patient physiological condition from the memory; compare the second patient physiological condition and the first patient physiological condition; and output a visual representation of the comparison between the second patient physiological condition and the first patient physiological condition to the display.

In an exemplary aspect, an ultrasound imaging system comprises: a processor circuit configured to: store, in a memory in communication with the processor circuit, a target parameter representative of a target anatomical scan window and a target probe orientation; receive an ultrasound image acquired by a ultrasound probe with an anatomical scan window and a probe orientation during an acquisition period; determine a parameter representative of the anatomical scan window and the probe orientation using a convolutional neural network; retrieve the target parameter from the memory; compare the target parameter and the parameter; and output a visual representation of the comparison to a display in communication with the processor circuit, wherein the visual representation of the comparison comprises: a first indicator when the target parameter and the parameter are the same; and a second indicator when the target parameter and the parameter are different.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
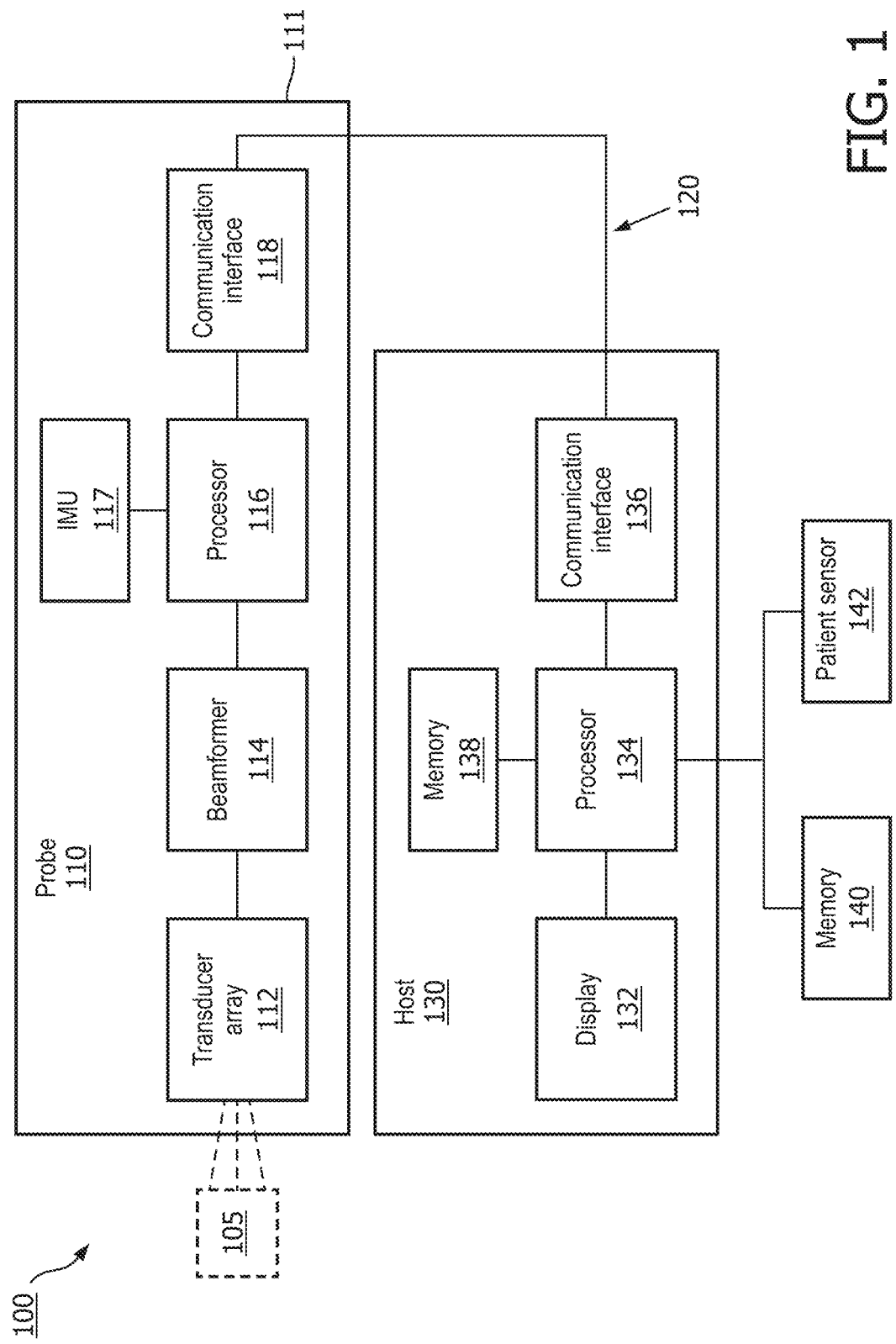
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the focusing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 may include a transducer array 112, a beamformer 114, a processor circuit 116, and a communication interface 118. The host 130 may include a display 132, a processor circuit 134, a communication interface 136, and a memory 138 storing patient information. The host 130 and/or the processor 134 of the host 130 may additionally be in communication with a memory 140, and a patient sensor 142.

In some embodiments, the probe 110 is an external ultrasound imaging device including a housing 111 configured for handheld operation by a user. The transducer array 112 can be configured to obtain ultrasound data while the user grasps the housing 111 of the probe 110 such that the transducer array 112 is positioned adjacent to or in contact with a patient's skin. The probe 110 is configured to obtain ultrasound data of anatomy within the patient's body while the probe 110 is positioned outside of the patient's body. In some embodiments, the probe 110 can be an external ultrasound probe and/or a transthoracic echocardiography (TTE) probe.

In other embodiments, the probe 110 can be an internal ultrasound imaging device and may comprise a housing 111 configured to be positioned within a lumen of a patient's body, including the patient's coronary vasculature, peripheral vasculature, esophagus, heart chamber, or other body lumen or body cavity. In some embodiments, the probe 110 may be an intravascular ultrasound (IVUS) imaging catheter or an intracardiac echocardiography (ICE) catheter. In other embodiments, probe 110 may be a transesophageal echocardiography (TEE) probe. Probe 110 may be of any suitable form for any suitable ultrasound imaging application including both external and internal ultrasound imaging.

In some embodiments, aspects of the present disclosure can be implemented with medical images of patients obtained using any suitable medical imaging device and/or modality. Examples of medical images and medical imaging devices include x-ray images (angiographic images, fluoroscopic images, images with or without contrast) obtained by an x-ray imaging device, computed tomography (CT) images obtained by a CT imaging device, positron emission tomography—computed tomography (PET-CT) images obtained by a PET-CT imaging device, magnetic resonance images (MRI) obtained by an MRI device, single-photon emission computed tomography (SPECT) images obtained by a SPECT imaging device, optical coherence tomography (OCT) images obtained by an OCT imaging device, and intravascular photoacoustic (IVPA) images obtained by an IVPA imaging device. The medical imaging device can obtain the medical images while positioned outside the patient body, spaced from the patient body, adjacent to the patient body, in contact with the patient body, and/or inside the patient body.

For an ultrasound imaging device, the transducer array 112 emits ultrasound signals towards an anatomical object 105 of a patient and receives echo signals reflected from the object 105 back to the transducer array 112. The ultrasound transducer array 112 can include any suitable number of acoustic elements, including one or more acoustic elements and/or a plurality of acoustic elements. In some instances, the transducer array 112 includes a single acoustic element. In some instances, the transducer array 112 may include an array of acoustic elements with any number of acoustic elements in any suitable configuration. For example, the transducer array 112 can include between 1 acoustic element and 10000 acoustic elements, including values such as 2 acoustic elements, 4 acoustic elements, 36 acoustic elements, 64 acoustic elements, 128 acoustic elements, 500 acoustic elements, 812 acoustic elements, 1000 acoustic elements, 3000 acoustic elements, 8000 acoustic elements, and/or other values both larger and smaller. In some instances, the transducer array 112 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) can be uniformly or independently controlled and activated. The transducer array 112 can be configured to obtain one-dimensional, two-dimensional, and/or three-dimensional images of a patient's anatomy. In some embodiments, the transducer array 112 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The object 105 may include any anatomy or anatomical feature, such as blood vessels, nerve fibers, airways, mitral leaflets, cardiac structure, abdominal tissue structure, appendix, large intestine (or colon), small intestine, kidney, liver, and/or any other anatomy of a patient. In some aspects, the object 105 may include at least a portion of a patient's large intestine, small intestine, cecum pouch, appendix, terminal ileum, liver, epigastrium, and/or psoas muscle. The present disclosure can be implemented in the context of any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, abdominal organs, and/or other systems of the body. In some embodiments, the object 105 may include malignancies such as tumors, cysts, lesions, hemorrhages, or blood pools within any part of human anatomy. The anatomy may be a blood vessel, as an artery or a vein of a patient's vascular system, including cardiac vasculature, peripheral vasculature, neural vasculature, renal vasculature, and/or any other suitable lumen inside the body. In addition to natural structures, the present disclosure can be implemented in the context of man-made structures such as, but without limitation, heart valves, stents, shunts, filters, implants and other devices.

The beamformer 114 is coupled to the transducer array 112. The beamformer 114 controls the transducer array 112, for example, for transmission of the ultrasound signals and reception of the ultrasound echo signals. In some embodiments, the beamformer 114 may apply a time-delay to signals sent to individual acoustic transducers within an array in the transducer 112 such that an acoustic signal is steered in any suitable direction propagating away from the probe 110. The beamformer 114 may further provide image signals to the processor circuit 116 based on the response of the received ultrasound echo signals. The beamformer 114 may include multiple stages of beamforming. The beamforming can reduce the number of signal lines for coupling to the processor circuit 116. In some embodiments, the transducer array 112 in combination with the beamformer 114 may be referred to as an ultrasound imaging component.

The processor 116 is coupled to the beamformer 114. The processor 116 may also be described as a processor circuit, which can include other components in communication with the processor 116, such as a memory, beamformer 114, communication interface 118, and/or other suitable components. The processor 116 may include a central processing unit (CPU), a graphical processing unit (GPU), a digital signal processor (DSP), an application specific integrated circuit (ASIC), a controller, a field programmable gate array (FPGA) device, another hardware device, a firmware device, or any combination thereof configured to perform the operations described herein. The processor 116 may also be implemented as a combination of computing devices, e.g., a combination of a DSP and a microprocessor, a plurality of microprocessors, one or more microprocessors in conjunction with a DSP core, or any other such configuration. The processor 116 is configured to process the beamformed image signals. For example, the processor 116 may perform filtering and/or quadrature demodulation to condition the image signals. The processor 116 and/or 134 can be configured to control the array 112 to obtain ultrasound data associated with the object 105.

The probe 110 can include an inertial measurement unit (IMU) 117, which is an electronic device that generates IMU data (e.g., specific force, angular rate, orientation, proper acceleration, angular velocity, etc.). The IMU 117 can include one or more accelerometers, gyroscopes, and/or magnetometers disposed within the housing 111 of the probe 110. The IMU data can be representative of the probe 110 during operation of the probe 110 to acquire ultrasound images.

The communication interface 118 is coupled to the processor 116. The communication interface 118 may include one or more transmitters, one or more receivers, one or more transceivers, and/or circuitry for transmitting and/or receiving communication signals. The communication interface 118 can include hardware components and/or software components implementing a particular communication protocol suitable for transporting signals over the communication link 120 to the host 130. The communication interface 118 can be referred to as a communication device or a communication interface module.

The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

At the host 130, the communication interface 136 may receive the image signals. The communication interface 136 may be substantially similar to the communication interface 118. The host 130 may be any suitable computing and display device, such as a workstation, a personal computer (PC), a laptop, a tablet, or a mobile phone.

The processor 134 is coupled to the communication interface 136. The processor 134 may also be described as a processor circuit, which can include other components in communication with the processor 134, such as the memory 138, the communication interface 136, and/or other suitable components. The processor 134 may be implemented as a combination of software components and hardware components. The processor 134 may include a central processing unit (CPU), a graphics processing unit (GPU), a digital signal processor (DSP), an application-specific integrated circuit (ASIC), a controller, an FPGA device, another hardware device, a firmware device, or any combination thereof configured to perform the operations described herein. The processor 134 may also be implemented as a combination of computing devices, e.g., a combination of a DSP and a microprocessor, a plurality of microprocessors, one or more microprocessors in conjunction with a DSP core, or any other such configuration. The processor 134 can be configured to generate image data from the image signals received from the probe 110. The processor 134 can apply advanced signal processing and/or image processing techniques to the image signals. In some embodiments, the processor 134 can form a three-dimensional (3D) volume image from the image data. In some embodiments, the processor 134 can perform real-time processing on the image data to provide a streaming video of ultrasound images of the object 105.

The memory 138 is coupled to the processor 134. The memory 138 may be any suitable storage device, such as a cache memory (e.g., a cache memory of the processor 134), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, solid state drives, other forms of volatile and non-volatile memory, or a combination of different types of memory.

The memory 138 can be configured to store patient information, measurements, data, or files relating to a patient's medical history, history of procedures performed, anatomical or biological features, characteristics, or medical conditions associated with a patient, computer readable instructions, such as code, software, or other application, as well as any other suitable information or data. The memory 138 may be located within the host 130. Patient information may include measurements, data, files, other forms of medical history, such as but not limited to ultrasound images, ultrasound videos, and/or any imaging information relating to the patient's anatomy. The patient information may include parameters related to an imaging procedure such as an anatomical scan window, a probe orientation, and/or the patient position during an imaging procedure. The patient may include data, images, metrics, or other information related to other imaging modalities, such as CT imaging. The memory 138 can also be configured to store information related to the training and implementation of deep learning networks (e.g., neural networks). Mechanisms for training and implementing the deep learning networks are described in greater detail herein.

Any or all of the previously mentioned computer readable media, such as patient information, code, software, or other applications, or any other suitable information or data may also be stored the memory 140. The memory 140 may serve a substantially similar purpose to the memory 138 but may not be located within the host 130. For example, in some embodiments, the memory may be a cloud-based server, an external storage device, or any other device for memory storage. The host 130 may be in communication with the memory 140 by any suitable means as described. The host 130 may be in communication with the memory 140 continuously or they may be in communication intermittently upon the request of the host 130 or a user of the ultrasound system 100.

The processor 134 of the host 130 may also be in communication with a patient sensor 142. The patient sensor 142 may monitor any suitable physiological characteristics of the patient being imaged by the imaging system 100. For example, the patient sensor 142 may acquire data related to a patient's heart rate, respirational rate, blood pressure, body temperature, or any other physiological metrics of the patient, or data related to the patient's positioning. Accordingly, the patient sensor 142 can be a heart rate sensor, respiration sensor, blood pressure sensor, temperature sensor, or orientation sensor etc. This information may be received by the processor 134 of the host 130 and used to minimize their impact on the images or data aquired by the system 100. The host 130 may be in communication with the patient sensor 142 by any suitable means as described. The host 130 may be in communication with the memory 142 continuously or they may be in communication intermittently upon the request of the host 130 or a user of the ultrasound system 100.

The host 130 may be in communication with the memory 140 and/or the patient sensor 142 via any suitable communication method. For example, the host 130 may be in communication with the memory 140 and/or the patient sensor 142 via a wired link, such as a USB link or an Ethernet link. Alternatively, the host 130 may be in communication with the memory 140 and/or the patient sensor 142 via a wireless link, such as an UWB link, an IEEE 802.11 WiFi link, or a Bluetooth link.

The display 132 is coupled to the processor circuit 134. The display 132 may be a monitor or any suitable display. The display 132 is configured to display the ultrasound images, image videos, and/or any imaging information of the object 105.

The system 100 may be used to assist a sonographer in performing an ultrasound scan. The scan may be performed in a at a point-of-care setting. In some instances, the host 130 is a console or movable cart. In some instances, the host 130 may be a mobile device, such as a tablet, a mobile phone, or portable computer. During an imaging procedure, the ultrasound system can acquire an ultrasound image of a particular region of interest within a patient's anatomy. The ultrasound system 100 may then analyze the ultrasound image to identify various parameters associated with the acquisition of the image such as the scan window, the probe orientation, the patient position, and/or other parameters. The system 100 may then store the image and these associated parameters in the memory 138 and/or the memory 140. At a subsequent imaging procedure, the system 100 may retrieve the previously acquired ultrasound image and associated parameters for display to a user which may be used to guide the user of the system 100 to use the same or similar parameters in the subsequent imaging procedure, as will be described in more detail hereafter.

In some aspects, the processor 134 may utilize deep learning-based prediction networks to identify parameters of an ultrasound image, including an anatomical scan window, probe orientation, patient position, and/or other parameters. In some aspects, the processor 134 may receive metrics or perform various calculations relating to the region of interest imaged or the patient's physiological state during an imaging procedure. These metrics and/or calculations may also be displayed to the sonographer or other user via the display 132.

Figure 2:
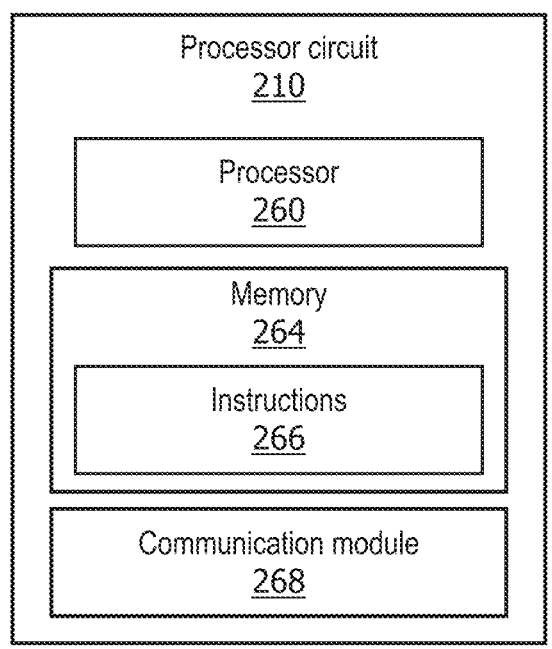
FIG. 2 is a schematic diagram of a processor circuit, according to aspects of the present disclosure.

FIG. 2 is a schematic diagram of a processor circuit, according to aspects of the present disclosure. The processor circuit 210 may be implemented in the probe 110, the host system 130 of FIG. 1, or any other suitable location. One or more processor circuits can be configured to carry out the operations described herein. The processor circuit 210 can be part of the circuitry 114 and/or circuitry 134, or may be separate circuitry. In an example, the processor circuit 210 may be in communication with the transducer array 112, circuitry 114, communication interface 122, communication interface 140, circuitry 134, and/or the display 132, as well as any other suitable component or circuit within ultrasound system 100. As shown, the processor circuit 210 may include a processor 260, a memory 264, and a communication module 268. These elements may be in direct or indirect communication with each other, for example via one or more buses.

The processor 260 may include a CPU, a GPU, a DSP, an application-specific integrated circuit (ASIC), a controller, an FPGA, another hardware device, a firmware device, or any combination thereof configured to perform the operations described herein. The processor 260 may also be implemented as a combination of computing devices, e.g., a combination of a DSP and a microprocessor, a plurality of microprocessors, one or more microprocessors in conjunction with a DSP core, or any other such configuration. The processor 260 may also include an analysis module as will be discussed in more detail hereafter. The analysis module may implement various deep learning networks and may be a hardware or a software implementation. The processor 260 may additionally include a preprocessor in either hardware or software implementation.

The memory 264 may include a cache memory (e.g., a cache memory of the processor 260), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 264 includes a non-transitory computer-readable medium. The memory 264 may store instructions 266. The instructions 266 may include instructions that, when executed by the processor 760, cause the processor 260 to perform the operations described herein with reference to the probe 110 and/or the host 130 (FIG. 1). Instructions 266 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements. Instructions 266 may include various aspects of a preprocessor, deep learning network, convolutional neural network (CNN) or various other instructions or code.

The communication module 268 can include any electronic circuitry and/or logic circuitry to facilitate direct or indirect communication of data between the processor circuit 710, the probe 110, and/or the display 132 and/or display 266. In that regard, the communication module 268 can be an input/output (I/O) device. In some instances, the communication module 268 facilitates direct or indirect communication between various elements of the processor circuit 210 and/or the probe 110 (FIG. 1) and/or the host 130 (FIG. 1).

Figure 3:
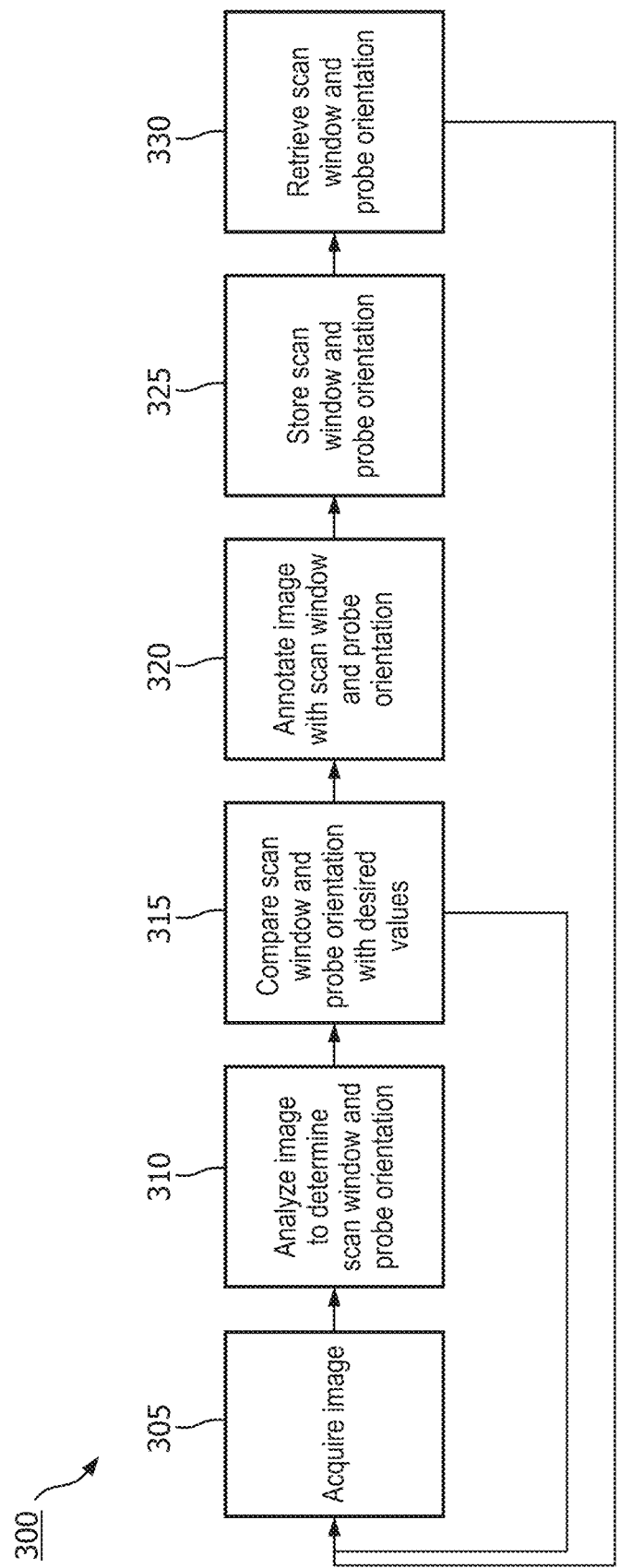
FIG. 3 is a flow diagram of a method of determining an anatomical scan window and/or probe orientation associated with an ultrasound image, according to aspects of the present disclosure.

FIG. 3 is a flow diagram of a method 300 of determining an anatomical scan window and/or probe orientation associated with an ultrasound image, according to aspects of the present disclosure. As illustrated, the method 300 includes a number of enumerated steps, but embodiments of the method 300 may include additional steps before, after, or in between the enumerated steps. In some embodiments, one or more of the enumerated steps may be omitted, performed in a different order, or performed concurrently. The steps of the method 300 can be carried out by any suitable component within the diagnostic system 100 and all steps need not be carried out by the same component. In some embodiments, one or more steps of the method 300 can be performed by, or at the direction of, a processor circuit of the diagnostic system 100, including, e.g., the processor 260 (FIG. 2) or any other component.

It is noted that the method 300 may include a process which may be applied multiple times and at different times, or only on a single occasion. In some embodiments, the method 300 may describe a process of identifying an anatomical scan window and/or probe orientation at one particular imaging procedure at one time point. In other embodiments, the method 300 may repeat at a subsequent imaging procedure to identify the scan window and/or probe orientation of images associated with the subsequent procedure and compare them to previous scan windows and/or probe orientations. It is additionally noted that the method 300 may also be used to identify and compare parameters in addition to only the scan window and/or probe orientation described in FIG. 3. For example, an additional parameter may include patient position as will be described in more detail hereafter. However, for simplicity's sake, the method 300 of FIG. 3 will be described as identifying and comparing only the scan window and/or probe orientation, through additional parameters may also be identified and compared.

At step 305, the method 300 includes acquiring an ultrasound image. At an ultrasound imaging procedure, the sonographer or user of the ultrasound imaging system 100 may grasp the probe 110 of any suitable type and direct it toward a region of interest of the patient's anatomy. When the sonographer is satisfied with the view, or when the region of interest is properly and adequately depicted by the ultrasound imaging system 100, the sonographer may acquire an image. In some embodiments, inertial measurement unit (IMU) data from the ultrasound probe, such as data from an accelerometer, gyroscope, or other similar device, may be additionally acquired at step 305 as will be discussed in more detail hereafter.

At step 310, the method 300 includes analyzing the acquired ultrasound image to determine an anatomical scan window and/or probe orientation. The ultrasound imaging system 100 may employ a deep learning network to determine the scan window and/or probe orientation based on the acquired ultrasound image. In some embodiments, the deep learning network may be a CNN. In other embodiments, the deep learning network may be any other suitable implementation of an artificial intelligence system or structure including, for example, a random forest deep learning approach, a regression analysis approach, or any other suitable approach or structure. The deep learning network may be trained prior to the initiation of the method 300 to identify a scan window and/or probe orientation associated with a given ultrasound image. This training will be described with more detail hereafter. The ultrasound imaging system may use the deep learning network to analyze the content of the acquired ultrasound image and determine from the image itself, the scan window and/or the probe orientation. This additional information is generally helpful to sonographers but infrequently captured and can vary greatly from procedure to procedure.

Within a patient anatomy, various structures of high density, such as bones or kidney stones, readily reflect acoustic waves and appear brightly in an ultrasound image. Whereas structures of less density reflect acoustic waves less and appear faintly in an ultrasound image or do not appear at all. A sonographer imaging a region of interest within a patient must not place the ultrasound imaging probe 110 such that a high-density structure is positioned between the probe 110 and the region of the interest as the high-density structure will obscure the region of interest within the final ultrasound image. Sonographers may therefore find anatomical scan windows, or areas of the anatomy through which a clear image of the region of interest may be acquired. As an example, a scan window may be intercostal, or between two ribs of the patient. In another application, the scan window may be subcostal, meaning the probe may be positioned below the ribs of the patient. The scan window may also be epigastric, lateral, parasagittal, flank, or any other suitable scan window depending on the region of interest to be imaged and the surrounding structures within the patient anatomy. The probe orientation may refer to the direction of the probe at the time an ultrasound image was acquired. Specifically, the probe orientation can be defined as the relative rotation between the patient coordinate system For example, the patient coordinate system may be defined using the right-left, superior-inferior, and anterior-posterior axes and the probe coordinate system may be defined using the long axis, the short axis, and the normal axis of the transducer array. The long axis of the transducer array may be defined as the axis along which conventional 2D images are generated with the probe. The short axis of the transducer array may be defined as the axis which is perpendicular to the long axis in the plane of the array. The normal axis may be defined as the axis perpendicular to the array plane. For example, the probe orientation may be in a lateral orientation, a transverse orientation, a longitudinal orientation, an oblique orientation, or in any other suitable orientation. At step 310, the scan window and/or the probe orientation may be estimated by the deep learning network.

At step 315, the method 300 includes comparing the anatomical scan window and/or probe orientation with desired values. In some ultrasound imaging settings, the desired values of the scan window and/or probe orientation at step 315 may be the scan window and/or probe orientation of an ultrasound image acquired at a previous ultrasound imaging procedure. The ultrasound system 100 may compare, for example, the scan window determined at step 310 of the acquired image with the scan window of a previously acquired image and determine if the scan window of the acquired image and the scan window of the previously acquired image are the same or differ. If these two scan windows differ, the system 100 may notify the user of the difference by a method including any suitable indicator. Similarly, the probe orientation determined at step 310 of the acquired image may be compared with the probe orientation of the same previously acquired image. The system 100 may determine if the probe orientation of the acquired image and the probe orientation of the previously acquired image are the same or differ. If these two probe orientations differ, the system 100 may notify the user of the difference by a method including another suitable indicator. As an example, at step 315, the imaging system 100 may determine that the both the scan window and the probe orientation of the acquired image differ from the scan window and the probe orientation of the previously acquired image. In such a scenario, the system 100 may identify the difference to the user and revert back to step 305 at which an additional image may be acquired. At step 310, the new image may be analyzed to determine a new scan window and probe orientation which may be again compared at step 315. In another scenario, the system 100 may determine that the scan windows of the acquired image and previously acquired image are the same but the probe orientations of these images differ. The system 100 may then indicate the difference in probe orientation only and revert back to step 305. Alternatively, the system 100 may determine that the probe orientations are the same, but the scan windows of the acquired image and previously acquired image differ. The system 100 may identify the difference in scan window only and revert to step 305. If, however, the system 100 determines that the scan window and probe orientation of the acquired image match the scan window and probe orientation of the previously acquired image, the system 100 may indicate that both parameters match and may proceed to step 320.

In some embodiments, in an initial ultrasound imaging procedure, in which no previous ultrasound image and corresponding parameters such as anatomical scan window and/or probe orientation are available, step 315 may not be performed. In some embodiments, in an initial ultrasound imaging procedure in which no previous ultrasound images and parameters are available, a recommended or target scan window and/or probe orientation may be supplied to the user of the imaging system 100. For example, in such a first ultrasound imaging procedure, the system may determine the desired parameters based on e.g., a user input selecting the desired scan window and/or probe orientation, a preset stored in memory and associated with scanning a particular anatomy, part of a physician's order for the ultrasound image stored in memory, etc. In some embodiments, the recommended or target scan window and/or probe orientation, which may also be referred to as target parameters, may be based on previous imaging procedures of different patients in which the same region of interest was imaged. The recommended or target parameters may be based on recommendations from experts in the field and may be stored in a memory in communication with the system 100 and retrieved based on an input relating to the region of interest to be imaged, a condition of the patient, or any other factors. In some embodiments, the recommended scan window and/or probe orientation may be based on images produced by other imaging modalities, such as by an x-ray, magnetic resonance imaging (MRI), and/or computed tomography (CT) scanner. For example, if the anatomy of a patient or a similar patient anatomy has been imaged with a CT scanner, the sonographer may use the data acquired by the CT scanner to determine a recommended scan window and/or probe orientation and may input their determined scan window and/or probe orientation into the system 100 for comparison at step 315. In circumstances in which no previous imaging acquisition was conducted to determine target parameters, but the target parameters are provided from other sources, they may be provided by a doctor, hospital, or other medical experts or healthcare provider or organization. For example, a doctor, hospital, or other medical experts or healthcare provider or organization may determine the target parameters as a standard or default protocol or preference based on any suitable data or circumstances. These target parameters may be input into the system 100 through a user input device such as a keyboard, mouse, touchscreen, via audible signals, or any other suitable input device or interface in communication with the processor circuit.

As shown by loop created by steps 305-315, the method 300 may guide the user of the system 100 to obtain an ultrasound image in a similar fashion as previously or use recommended scan windows and/or probe orientations to enable the best possible comparison. In this way, changes to the region of interest may be more easily and accurately observed over longitudinal studies and/or imaging procedures.

At step 320, the method 300 includes annotating the image with the anatomical scan window and/or probe orientation. After the scan window and/or probe orientation of the acquired image match the desired values at step 315, the method 300 may annotate the acquired ultrasound image with the determined scan window and/or probe orientation. Annotating the image can include graphically overlaying alphanumeric text and/or symbols on the ultrasound image itself such that the text and/or symbols are visible with the image. Annotating the image can additionally or alternatively include associating data representative of the anatomical scan window and/or probe orientation with the image (e.g., metadata of the image and/or data in the image file header). Accordingly, annotating the ultrasound image need not to include providing the scan window and/or probe orientation such that it is displayed on the image. In some embodiments, although the scan window and/or probe orientation do not match the desired values, a user of the system 100 may direct the system to proceed to step 320 anyway and annotate the acquired image with the new scan window and/or probe orientation. In other scenarios, the user of the system 100 may also direct the system to revert to step 305 to acquire, analyze, and compare an additional image even if the scan window and/or probe orientation do match the desired values.

At step 325, the method 300 includes storing the anatomical scan window and/or probe orientation in a memory. The scan window and/or probe orientation of the newly acquired ultrasound image may be stored in conjunction with the ultrasound image itself such that when it is retrieved at a later time, the image may be displayed along with its corresponding scan window and/or probe orientation. Data representative of the scan window and/or probe orientation and data representative of the image can be associated based on additional data stored in memory that links the data representative of the scan window and/or probe orientation and data representative of the image. The ultrasound image, corresponding scan window and/or probe orientation, as well as linking data, may be stored in any suitable location. For example, the image, scan window, and/or probe orientation may be stored in the memory 138 within the host 130 itself. In other embodiments, the image, scan window, and/or probe orientation may be stored in the memory 140 in communication with but spaced from the host 130. In other embodiments, the data may be stored on both the memory 138 and the memory 140.

At step 330, the method 300 includes retrieving the anatomical scan window and/or probe orientation. The processor circuit can retrieve the scan window and/or probe orientation along with the ultrasound image (or vice versa) because they are associated in memory. In some embodiments, the scan window and/or probe orientation stored in conjunction with the acquired image at step 325 may be designated as the desired values of step 315 in a subsequent imaging procedure. In this way, step 330 may be performed at a subsequent imaging procedure or may be performed at the close of the same procedure described previously. As shown by the arrow leading from step 330 to step 305, the process described by the method 300 may be performed iteratively. The method 300 may be performed with the same patient multiple times consecutively at a single imaging procedure or point of care scenario or may be performed at different times or at different imaging procedures.

Figure 4:
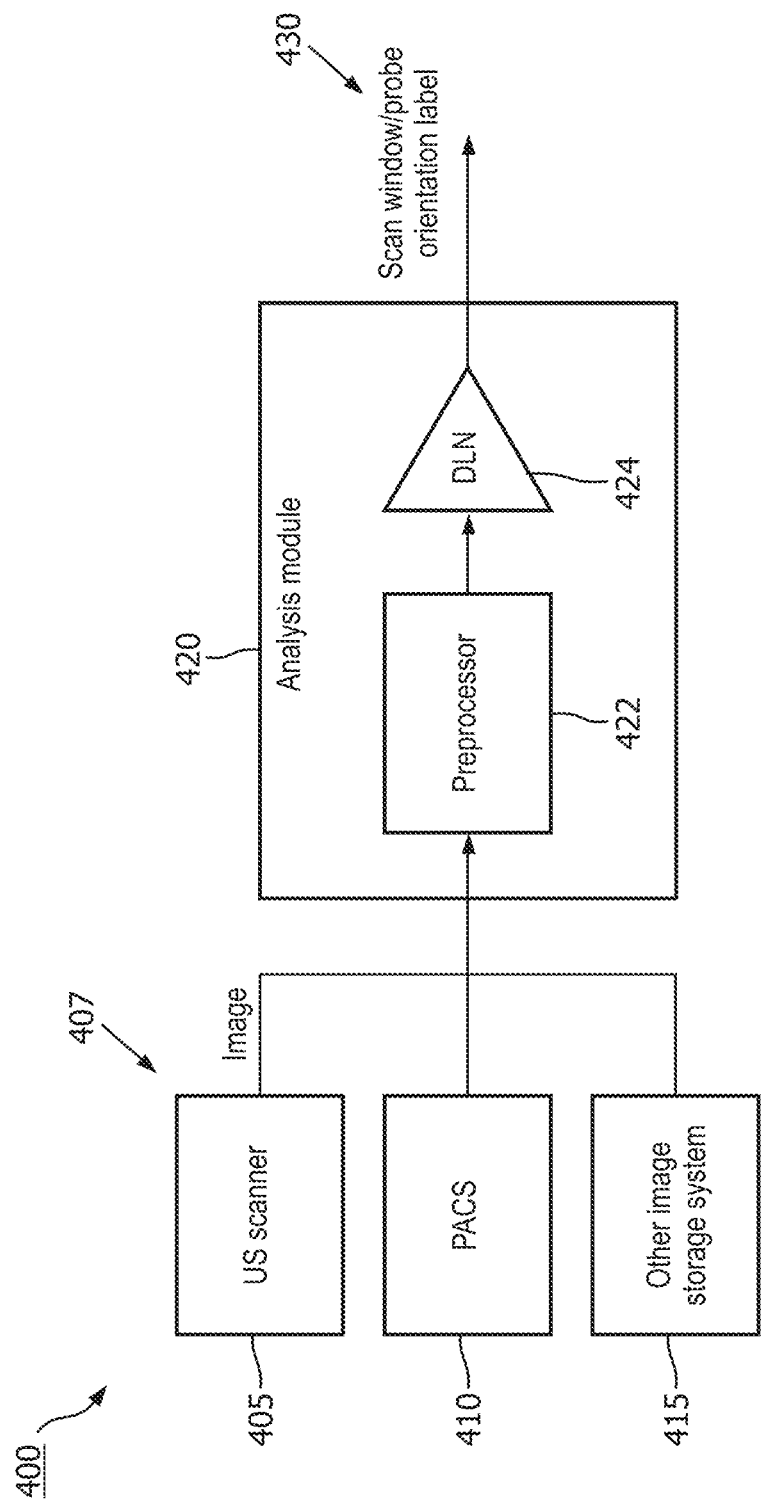
FIG. 4 is a schematic diagram of an ultrasound imaging system with a deep learning network, according to aspects of the present disclosure.

FIG. 4 is a schematic diagram of an ultrasound imaging system 400 with a deep learning network, according to aspects of the present disclosure. The system 400 can also be referenced as an artificial intelligence framework. In that regard, the artificial intelligence framework 400 may include a deep learning network and various aspects of the framework may be performed by the processor 134, the processor circuit 210, and/or may include instructions similar to the instructions 266 previously described. The embodiment of the artificial intelligence framework 400 shown in FIG. 4 includes various input images 407 received from various sources such as an ultrasound scanner 405, a picture archiving and communication system (PACS) 410, or other image storage system 415. The framework 400 may include an analysis module 420 with a preprocessor 422 and a deep learning network 424. In some embodiments, the analysis module 420 can be implemented in the host 130 (FIG. 1) and/or the processor circuit 210 (FIG. 2). The artificial intelligence framework 400 may generate a label 430 as an output. The deep learning network 400 may be trained to identify a plurality of organs within the patient anatomy or any other structure or may process images originating from a plurality of organs. In some embodiments, the deep learning network 400 may also be or include multiple deep learning networks, each trained to identify one organ within the patient anatomy or one structure or may process images originating from a single organ.

The input images 407 may be ultrasound images depicting a region of interest within a patient anatomy. The input images 407 may include any suitable number of ultrasound images. For example, the input images 407 may include only a single ultrasound image or may include multiple including, tens, hundreds, or thousands of ultrasound images as well as any number higher or lower. The input images 407 can be an image stream of frames continuously acquired (e.g., in real time) by an ultrasound imaging probe. The input images 407 can transmitted from the scanner 405 (e.g., a memory of the scanner 405) to the analysis module 420 as the images are being acquired or after the images are acquired. The input ultrasound images 407 may include images captured with any suitable scan window and/or probe orientation. For example, the images 407 may include a set of images showing the region of interest from one angle, another set of images from a different angle, and so on. The input images 407 may be of any suitable type or file format, and of any suitable size or resolution.

The input images 407 may be received by the analysis module 420 directly from the ultrasound scanner 405. The ultrasound scanner 405 may be or have features substantially similar to the probe 110, the transducer array 112, and/or host 130 (FIG. 1). The input images 407 received from the ultrasound scanner 405 may have been acquired by the ultrasound scanner 405 at any time. For example, the ultrasound scanner 405 may acquire several input images 407 at the direction of a user of the system 100 or otherwise and immediately transmitted to the analysis module 420. In other situations, the ultrasound scanner 405 may transmit input images 407 to the analysis module 420 from a previous imaging procedure.

The input images 407 may also be received by the analysis module 420 from the PACS 410. The PACS 410 may include the memory 138 of FIG. 1, the memory 140 of FIG. 1, the memory 264 of FIG. 2, or any other suitable components described. The PACS 410 may store multiple files or other data related to one or more patients. The PACS 410 may include wired or wireless storage devices such as servers, portable forms of media storage, or any other form of media storage. The PACS 410 may contain patient information from multiple patients and multiple imaging examinations and/or other medical examinations or procedures. In some embodiments, the PACS 410 may transmit any suitable number of input images 407 to the analysis module 420 upon request by the analysis module 420 and/or a user of the system 100. The PACS 410 may transmit input images 407 from various previous imaging procedures of any patient. In some embodiments, the input images 407 may be ultrasound images depicting the same region of interest within the same patient to be imaged at a present procedure or may be images depicting other regions of the same patient or different patients depending on the application and needs of the sonographer and/or patient.

As shown by the other image storage system 415, the analysis module 420 may additionally receive input images 407 other sources as well. For example, the other image storage system 415 may be a portable media storage device such as a secure digital storage device, a universal serial bus storage device, a compact disc, or any other form of portable media storage. The other storage system 415 may also include cloud-based storage implementations.

The analysis module 420 can include a preprocessor 422, which can include hardware (e.g., electrical circuit components) and/or software algorithms (e.g., executed by a processor). The preprocessor 422 may perform various functions to adjust, filter, or otherwise modify received input images 407 before transmitting the input images 407 to the deep learning network 424. For example, the preprocessor 422 may manipulate incoming images. The preprocessor 422 may perform various image processing steps for both training and prediction purposes. The preprocessor 422 may perform various tasks such as changing the contrast of the image, size of the image, resolution orientation, geometry, cropping, spatial transformation, resizing, normalizing, histogram modification or various other procedures to assist deep learning network 424 to work more efficiently or accurately.

The preprocessor 422 may also buffer and filter incoming images 407 and provide as an output a subset of the incoming images 407 that pass the buffer or filter. For example, the preprocessor 422 may determine a similarity metric (such as normalized correlation coefficient) between input images 407 received and buffered, and discard images that are too similar to other images in the buffer. In this way, the preprocessor 422 may measure the correlation between received input images 407 and quantify similarities with the similarity metric. The preprocessor 422 may be configured to compile input images 407 that have met the similarity metric threshold until a threshold number of N input images 407 is reached. Each time there are N images 407 stored at the preprocessor that have passed the similarity criteria, the group or subset may be passed on to the deep learning network 424 for processing, and the oldest image may be discarded.

The use of more than a single input image 407 may enhance identification of a region of interest within the patient anatomy. By selecting multiple input images 407 with sufficient distinction from one another and transmitting them to the deep learning network, the deep learning network 424 may produce a more robust estimate of the anatomical scan window, probe orientation, patient position, and/or other parameters. The number of input images 407 transmitted to the deep learning network 424 in a single group or subset may be any suitable number. For example, the preprocessor may transmit a single image 407, or may transmit 2, 3, 4, 10, 100, or more images 407 or any number therebetween. The process of selecting and transmitting input images 407 may occur at a training phase or an inference phase of the framework 400 shown.

In some embodiments, the preprocessor 422 may additionally identify any structures depicted in the current image using image processing techniques, deep learning network techniques, or any other suitable techniques. The preprocessor 422 may identify structures within an ultrasound image using some features similar to those described in U.S. Pat. No. 10,424,044, titled "Anatomically intelligent echocardiography for point-of-care"; U.S. Pat. No. 7,794,398, titled "Real-time volumetric bi-plane ultrasound imaging and quantification"; U.S. Pat. No. 8,698,795, titled "Interactive image segmentation"; U.S. Pat. No. 7,117,026, titled "Physiological model based non-rigid image registration"; U.S. Pat. No. 10,290,076, titled "System and method for automated initialization and registration of navigation system"; U.S. Pat. No. 8,144,950, titled "Method for facilitating post-processing of images using deformable meshes"; and U.S. Pat. No. 10,709,425, titled "3D ultrasound imaging system," all of which are hereby incorporated by reference in their entireties. The structures may be anatomy within the patient's body, such as organs. In some embodiments, the deep learning network 424 may include multiple artificial intelligence networks each trained to identify parameters of ultrasound images of various common structures within a patient anatomy. After identification of the imaged structure, the preprocessor may transmit an input image 407 to the appropriate corresponding deep learning network. For example, if a set of input images 407 analyzed at the preprocessor 422 depict a liver, the preprocessor 422 may determine similarity metrics between the input images 407 and select a subset of the input images 407 that are sufficiently distinct from one another and transmit the images 407 to a deep learning network 424 trained to identify parameters of ultrasound images depicting a liver. Similarly, a filtered subset of images 407 depicting a heart may be transmitted to a deep learning network 424 trained for images depicting a heart. In other embodiments, a single deep learning network 424 may identify image parameters of an ultrasound image regardless of any structure depicted in the image.

The deep learning network 424 may receive as an input the subset of images 407 modified and filtered by the preprocessor 422. The deep learning network 424 can include hardware (e.g., electrical circuit components) and/or software algorithms (e.g., executed by a processor). The deep learning network 424 may then identify various parameters associated with the received ultrasound images 407 as will be described with more detail hereafter. The parameters identified by the deep learning network 424 may include the anatomical scan window of the ultrasound probe, the orientation of the probe, the patient position at the time of imaging, and/or other parameters. In some embodiments, the deep learning network 424 may receive other inputs, such as IMU data or physiological measurements of the patient in addition to input images 407. These additional inputs may be received from the preprocessor 422, directly from the probe 110 (FIG. 1) or the patient sensor 142 (FIG. 1), or from any other suitable source. In some embodiments, the deep learning network 424 may determine a scan window, probe orientation, and/or patient position associated with each input image 407. In other embodiments, the deep learning network 424 may determine a scan window, probe orientation, and/or patient position associated with a subset of input images 407 rather than each image individually. The deep learning network 424 may be of any suitable form or type as previously described.

The deep learning network 424 may generate a label 430 as an output reflecting the parameters of the input image 407 or subset of input images 407 including an anatomical scan window, probe orientation, and/or patient position. The label 430 may be of any suitable type. For example, the label may include a visual representation such as any alpha-numeric text of any type or length, symbols, images, or any other representation. In addition, the label may include any suitable audio, or any other method of communicating to a user of the system the determined parameters. The output 430 can be transmitted from the analysis module 420 to a display and/or a memory (e.g., display or memory that is part of or in communication with the scanner 405, PACS 410, and/or storage 415).

The deep learning network 424 can include a convolutional neural network (CNN) in some embodiments. For example, the CNN can be or include a multi-class classification network, or an encoder-decoder type network. In some instances, the analysis module can implement a random forest algorithm instead of a deep learning network.

Figure 5:
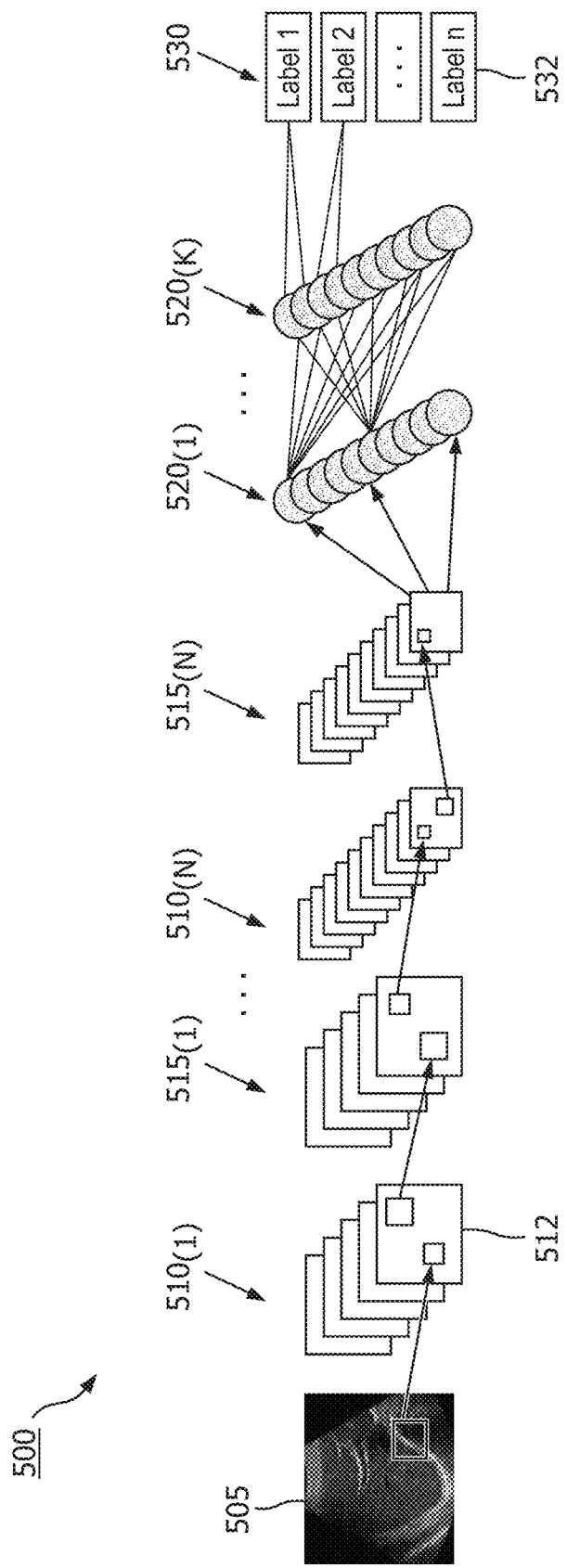
FIG. 5 is a schematic diagram of a convolutional neural network (CNN) configuration, according to aspects of the present disclosure.

FIG. 5 is a schematic diagram of a convolutional neural network (CNN) configuration 500, according to aspects of the present disclosure. For example, the CNN configuration 500 can be implemented as the deep learning network 424 (FIG. 4). In an embodiment, the configuration 500 may perform a classification task. The configuration 500 may be of any suitable type and may include any suitable type or number of layers including but not limited to convolutional layers, fully connected layers, flatten vectors, or any other techniques or implementations of artificial intelligence systems. The embodiments shown and/or described with reference to FIG. 5. can be scaled to include any suitable number of CNNs (e.g., about 2, 3 or more). The configuration 500 can be trained for identification of various anatomical scan windows, probe orientations, and/or patient positions associated with received ultrasound images as described in greater detail below.

The CNN may include a set of N convolutional layers 510 where N is any positive integer, each layer followed by a pooling layer 515. The CNN may also include a set of K fully connected layers 520, where K may be any positive integer. In one embodiment, the fully connected layers 520 include at least two fully connected layers 520. The convolutional layers 510 are shown as $510_{(1)}$ to $510_{(N)}$. The pooling layers 515 are shown as $515_{(1)}$ to $515_{(N)}$. The fully connected layers 520 are shown as $520_{(1)}$ to $520_{(K)}$. Each convolutional layer 510 may include a set of filters 512 configured to extract features from an input 505 (e.g., ultrasound images or other additional data). The convolutional layers 510 may include convolutional kernels of different sizes and strides. The values N and K and the size of the filters 512 may vary depending on the embodiments. In some instances, the convolutional layers $510_{(1)}$ to $510_{(N)}$, the pooling layers $515_{(1)}$ to $515_{(N)}$, and the fully connected layers $520_{(1)}$ to $5200_{(4)}$ may utilize a sigmoid, rectified non-linear (ReLU), leaky ReLU, softmax, or hyperbolic tangent activation function. The pooling layers 515 may include max pooling or average pooling techniques. The fully connected layers 520 may gradually shrink the high-dimensional output to a dimension of the prediction result (e.g., the classification output 530). Thus, the fully connected layers 520 may also be referred to as a classifier. In some embodiments, the fully convolutional layers 510 may additionally be referred to as perception or perceptive layers.

The fully connected layers 520 may downsample and map received information to a finite number of classes 532. In an embodiment, the final fully connected layer $520_{(K)}$ may be followed by a final classification layer such as softmax to transform the net activations in the final output layer to a series of values that can be interpreted as probabilities.

The classification output 530 may indicate a confidence score or probability for each of a plurality of classes 532, based on the input image 505. In that regard, the CNN 500 can be a multi-class classification network. In an exemplary embodiment, the plurality of classes 532 are each a combination of a scan window and a probe orientation, as shown in Table 1 below. Label 1 may be one such combination (e.g., right subcostal transverse), label 2 is another combination (e.g., Right subcostal longitudinal), and so on. The output 530 indicates how likely the input image 505 belongs to a particular class 532. For example, a high confidence score for label 1 and lower confidence scores for the other labels indicates that the output label of the CNN 1400 for the input image 505 is label 1 (right subcostal transverse). The confidence score may be of any suitable type. In one embodiment, the confidence score may be a probability (e.g., a decimal value between 0 and 1). In this way, the output of the CNN may be a likelihood value for each of the possible options. The option with the highest likelihood will be assigned to the image. In some instances, the highest likelihood value is compared to a threshold and the output label is assigned to the image if the value satisfies the threshold. For example, if the highest likelihood value exceed a minimum threshold, then the output label is assigned to the image. If the highest likelihood value is below the minimum threshold, no option will be selected or assigned, or a dedicated "unknown" label will be assigned. If the image is stored/archived, the label can be stored together with the image, for example in the DICOM header.

In an embodiment in which the deep learning network includes an encoder-decoder network, the network may include two paths. One path may be a contracting path, in which a large image, such as the image 505, may be convolved by several convolutional layers 510 such that the size of the image 505 changes in depth of the network. The image 505 may then be represented in a low dimensional space, or a flattened space. From this flattened space, an additional path may expand the flattened space to the original size of the image 505. In some embodiments, the encoder-decoder network implemented may also be referred to as a principal component analysis (PCA) method. In some embodiments, the encoder-decoder network may segment the image 505 into patches.

In some embodiments, the output label generated by the deep learning network may be in the form of an ordinal (1, 2, 3, etc.) representing both the anatomical scan window and probe orientation used during the acquisition of the input image 505. The ultrasound imaging system 100 may access a database or table correlating an ordinal value with a scan window and probe orientation combination. An example of some ordinal labels and corresponding scan window and probe orientation combinations is shown in Table 1 below:

TABLE 1

Exemplary labels assigned to scan windows and probe orientations

| Label | Corresponding Scan Window and Probe Orientation |
|---|---|
| 1 | Right subcostal transverse |
| 2 | Right subcostal longitudinal |

TABLE 1-continued

Exemplary labels assigned to scan windows and probe orientations

| Label | Corresponding Scan Window and Probe Orientation |
|---|---|
| 3 | Right subcostal oblique |
| 4 | Right intercostal transverse |
| 5 | Right intercostal longitudinal |
| 6 | Right intercostal oblique |
| 7 | Left subcostal transverse |
| 8 | Left subcostal longitudinal |
| 9 | Epigastric transverse |
| 10 | Epigastric longitudinal |
| 11 | Right lateral longitudinal |
| ... | ... |

Table 1 may correspond to possible scan windows and probe orientations for imaging one particular structure or region of interest within a patient anatomy, such as a liver. In some embodiments, the ultrasound imaging system 100 may access multiple tables similar to Table 1 associating ordinal labels with corresponding scan windows and probe orientations. Each table may correspond to a different structure or region of interest within a patient anatomy. In embodiments in which a separate deep learning network is trained for a single region of interest, each deep learning network may retrieve information from a single lookup table associated with that region of interest. In an embodiment in which a single deep learning network is trained for multiple regions of interest, the deep learning network may access different lookup tables depending on the region of interest imaged. In still other embodiments, a single lookup table may correspond to all regions of interest to be imaged.

In some embodiments, two CNNs can be implemented to respectively identify scan window and probe orientation. In such instances, the respective outputs of the CNNs are two distinct values, such as two separate ordinal labels respectively corresponding to a scan window and a probe orientation. An example of a table corresponding separate scan window labels and probe orientation tables is shown in Table 2 below:

TABLE 2

Exemplary labels assigned to scan windows and labels assigned to probe orientations

| Scan Window Label | Corresponding Scan Window | Probe Orientation Label | Corresponding Probe Orientation |
|---|---|---|---|
| 1 | Right subcostal | 101 | Transverse |
| 2 | Right intercostal | 102 | Oblique |
| 3 | Left subcostal | 103 | Longitudinal |
| 4 | Epigastric | ... | ... |
| 5 | Right lateral | | |
| ... | ... | | |

In another embodiment, a single CNN can be implemented to identify scan window and probe orientation in two separate sets of labels. In such instances, the last fully connected layer $520_{(k)}$ may be connected to two separate sets of classification outputs $530_{(1)}$ and $530_{(2)}$, each with their own sets of labels $532_{(1)}$ and $532_{(2)}$, in which $532_{(1)}$ may correspond to scan window labels $532_{(2)}$ and may correspond to probe orientation labels.

In an additional embodiment, the probe orientation may be predicted or estimated as three continuous variables representing the probe rotation relative to the patient's standard coordinate system, rather than limiting the probe orientation to discrete values represented by an ordinal label. The patient's standard coordinate system may be defined by three axes: right-left, anterior-posterior, and cranio-caudal. The position of the probe at the time of image acquisition may then be determined relative to the patient coordinate system. This orientation determination may be made using IMU data or optical image data. In an embodiment in which IMU data is received from the ultrasound probe, the ultrasound probe may be equipped with orientation measurement tools such as an accelerometer, gyroscope, or other measurement tool to determine the probe orientation relative to a gravity vector. This orientation may then be converted to the patient axes depending on the patient position. The probe orientation as a continuous three value coordinate may also be determined based on an optical camera image taken at the time of ultrasound image acquisition. Various image processing techniques may be used to estimate the probe orientation relative to the patient's coordinate system. The estimated probe orientation coordinates may also be fine-tuned at a time after the ultrasound image acquisition. For example, the optical camera image may be stored within a memory 138 or memory 140 and associated with the acquired ultrasound image for later review. Additional details regarding probe orientation relative to patient position will be described in more detail hereafter.

Figure 6:
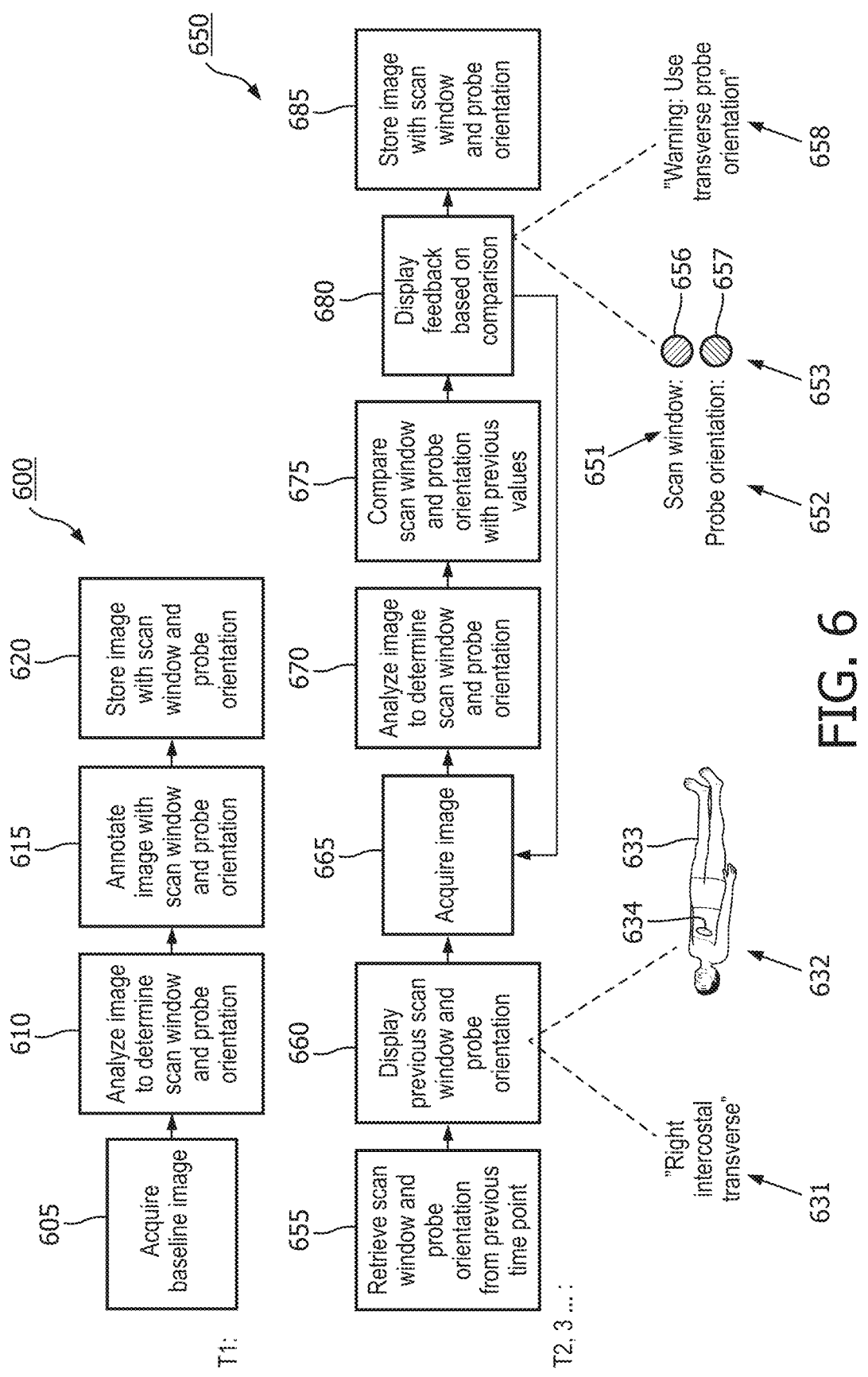
FIG. 6 is a flow diagram for a method of analyzing an ultrasound image from an imaging procedure and a flow diagram for a method of analyzing and comparing ultrasound images from an additional imaging procedure, according to aspects of the present disclosure.

In embodiments in which the probe orientation is estimated as a continuous three-value coordinate, the deep learning network 500 shown in FIG. 5 may include a regression task. For example, the fully connected layers 520 may perform a regression task. In some embodiments, the deep learning network may output one continuous three-value coordinate corresponding to orientation and a second continuous three-value coordinate correspond to translation, as well as any other coordinates relating to the position of the probe at the time of image acquisition. Determining the probe orientation as a continuous variable may utilize some features similar to those described in P.C.T. Application No. PCT/EP2020/081548, titled "Ultrasound Screening Coverage Tool," and filed Nov. 10, 2020, which is hereby incorporated by reference in its entirety. Determining the probe orientation as a continuous variable may also utilize some features similar to those described in E.P. Application No. 20150464.4, titled "Patient Model Estimation for Interventions," and filed Jan. 7, 2020, which is also hereby incorporated by reference in its entirety FIG. 6 is a flow diagram for a method 600 of analyzing an ultrasound image from an imaging procedure and a flow diagram for a method 650 of analyzing and comparing ultrasound images from an additional imaging procedure, according to aspects of the present disclosure. As illustrated, the methods 600 and 650 includes a number of enumerated steps, but embodiments of the method 600 may include additional steps before, after, or in between the enumerated steps. In some embodiments, one or more of the enumerated steps may be omitted, performed in a different order, or performed concurrently. The steps of the methods 600 and 650 can be carried out by any suitable component within the diagnostic system 100 and all steps need not be carried out by the same component. In some embodiments, one or more steps of the methods 600 and 650 can be performed by, or at the direction of, a processor circuit of the diagnostic system 100, including, e.g., the processor 260 (FIG. 2) or any other component.

At step 605, the method 600 includes acquiring a baseline ultrasound image. As shown, steps 605 through 620 may be performed at a time point T1. At time point T1, a baseline ultrasound image may be acquired. This baseline may be associated with an anatomical scan window and/or probe orientation. The scan window and/or probe orientation may be selected by a user of the ultrasound imaging system 100 based on a scan window and/or probe orientation recommended for imaging of the particular region of interest. The scan window and/or probe orientation may also be made based on an imaging plan determined by the user of the system 100 or may be arbitrarily chosen.

At step 610, the method 600 includes analyzing the acquired ultrasound image to determine the anatomical scan window and/or probe orientation. At step 610, the scan window and/or probe orientation label may be automatically generated using the deep learning network techniques previously described. The ultrasound imaging system may use the deep learning network to analyze the content of the acquired ultrasound image and determine from the image itself, the scan window and/or the probe orientation.

At step 615, the method 600 includes annotating the acquired ultrasound image with the anatomical scan window and/or probe orientation. Annotation of an ultrasound image may be done in any suitable way. For example, visual representations such as alpha-numeric text or graphical representations may be embedded within an acquired ultrasound image or created as a separate data and associated with the ultrasound image.

At step 620, the method 600 includes storing the acquired ultrasound image with the anatomical scan window and/or probe orientation. The ultrasound image and scan window and/or probe orientation may be stored on any suitable media storage device including the memory 138 within the host 130 or the memory 140 (FIG. 1). The ultrasound image and scan window and/or probe orientation may also be stored in the PACS 410 (FIG. 4).

FIG. 6 also illustrates the method 650. The steps of the method 650 may be performed after the steps of the method 600 are performed. For example, the method 600, including steps 605 through 620, may be performed at a time point T1. The method 650, including steps 655 through 685 as shown, may be performed at a time point T2, a time point after T1. The steps 655 through 685 of the method 650 may also be performed any number of times, including at an additional time point T3 after T2, a time point T4 after T3, and so on. In some embodiments, the imaging procedures of time point T1, T2, T3, etc. shown in FIG. 6 illustrate a longitudinal study of a region of interest within a patient. In particular, the same region of interest imaged at time point T1 according to method 600 may be imaged at subsequent time points according to method 650. Such a longitudinal study may allow a sonographer or physician to monitor changes to a region of interest over long periods of time. Any length of time may pass between consecutive imaging procedures according to the methods 600 and 650. For example, the time between two imaging procedures could be minutes, hours, days, weeks, months, or years.

At step 655, the method 650 includes retrieving the anatomical scan window and/or probe orientation of a previous imaging procedure at a previous time point. In some embodiments, the scan window and/or probe orientation, as well as the patient position and/or other parameters depending on the application, may be the same scan window, probe orientation, and/or other parameters stored at step 620 of the method 600 previously described. The scan window and/or probe orientation retrieved at step 655 may become the desired values or target values of the procedure described by the method 650.

At step 660, the method 650 includes displaying the previous anatomical scan window and/or probe orientation. The scan window and/or probe orientation may be communicated to the sonographer by any suitable method. For example, the scan window and/or probe orientation may be displayed as a visual representation. Specifically, they could be displayed as form of alpha-numeric text or as a graphical representation such as a symbol or image. The scan window and/or probe orientation may also be communicated to the sonographer via audio. An example of alpha-numeric text 631 is shown in relation to step 660 in FIG. 6. Such alpha-numeric text may indicate the scan window, such as "right intercostal" as shown, or any other scan window, as well as the probe orientation, such as "transverse" as shown, or any other probe orientation. The probe orientation may alternatively or additionally be displayed as a three-value continuous coordinate as previously described. The scan window and/or probe orientation may additionally or alternatively be shown as a graphical representation similar to the graphical representation 632. The graphical representation 632 may include a depiction of a patient 633. In some embodiments, the position of the patient 633 may be displayed visually via the depiction of the patient 633, such that a sonographer may recognize that the patient was in a supine position, as an example, at the time of previous imaging. The system 100 may also display the patient position via alpha-numeric text in conjunction with the alpha-numeric text 631 or may convey the position via any other symbols, audio, or other means. The graphical representation may also include an indicator 634. The indicator 634 may convey a scan window and/or probe orientation to the sonographer. The indicator 634 may be shown in conjunction with the patient 633. The indicator 634 may indicate a location on the patient's body corresponding to the scan window and/or patient position. The indicator may be or include any suitable symbol, color, alpha-numeric text, pattern, or any other feature to specify information to the sonographer.

At step 665, the method 650 includes acquiring an additional ultrasound image. The sonographer may use the anatomical scan window, probe orientation, and/or patient position displayed at the step 660 to position the ultrasound probe in a similar location to the location of the probe at the previous imaging procedure and may acquire an image. In some embodiments, the imaging system including the probe used to acquire the image at step 665 may be the same imaging system and probe as was used to acquire the previous image at step 605 or the sonographer may use a different imaging system and/or probe at step 665 as was used previously at step 605. In some embodiments, the step 660 of the method 650 may not be performed before the step 665. For example, a sonographer may acquire an image without any direction or indication of the previous scan window, probe orientation, and/or patient position. In some embodiments, the sonographer may choose to retrieve and view previous scan windows, probe orientations, and/or patient positions or may not.

At step 670, the method 650 includes analyzing the additional ultrasound image to determine an anatomical scan window and/or probe orientation. The system 100 may use any suitable deep learning network, such as the network 424 of FIG. 4 or the structure described with reference to FIG. 5 to automatically identify image parameters such as the scan window, probe orientation, and/or patient position of the image based on the acquired ultrasound image. The step 670 of analyzing the ultrasound image acquired at the step 665 may include any of the features previously described with reference to step 310 of method 300 or step 610 of method 600.

At step 675, the method 650 includes comparing the anatomical scan window and/or probe orientation of the additional ultrasound image to the scan window and/or probe orientation of a previous ultrasound image. The scan window, probe orientation, and/or patient position estimated at step 670 may be compared with the scan window, probe orientation, and/or patient position retrieved at step 655. The system 100 may determine whether the scan window of the image acquired at the current time point matches the scan window acquired at time point T1 and similarly compare the probe orientation and patient position from the different time points.

At step 680, the method 650 includes displaying to a user feedback based on the comparison of the anatomical scan window and/or probe orientation of the additional ultrasound image to the scan window and/or probe orientation of a previous ultrasound image. Any suitable indicator may be used to convey the comparison results to the sonographer. For example, any of the previously mentioned communication methods may be used. If the labels corresponding to any of the parameters of the image differ, the indicator may include a warning to be communicated to the sonographer. The indicator may indicate which parameters are the same and which parameters differ. For example, the scan window of the image acquired at the current imaging procedure may differ from the procedure of time point T1, but the probe orientation of the current procedure and previous procedure may match. As shown by the visual representation 651 shown in FIG. 6 in relation to step 680, a visual representation 651 displaying feedback based on the comparison of the parameters may include text 652 related to the parameters analyzed and indicators 653 associated with each parameter. For example, if the scan window of the current image matches the scan window of the previous image retrieved at step 655, an indicator 656 may be displayed. The indicator 656 may be of a distinct color, pattern, shape, or have any other visual characteristics indicating that the scan windows match. If, for example, the probe orientation of the current image differs from the previous probe orientation retrieved at step 655, and indicator 657 may be displayed. The indicator may also be of any color, pattern, shape, or other visual characteristics, but may differ from indicator 656 to differentiate the two. In some embodiments, the visual representation 651 may also include text and/or indicators relating to a patient position and similarities or differences in the current patient position and patient position of previous procedures. At step 680, the system 100 may additionally or alternatively display alpha-numeric text such as text 658 to convey whether differences exist in parameters of the current ultrasound image and the previous ultrasound image as shown.

In the event that one or more parameters of the current ultrasound image acquired at step 665 differ from any of the parameters of the previous ultrasound image retrieved at step 655, the method may revert back to step 665, as shown by the arrow. At step 665, the sonographer may adjust the positioning of the ultrasound probe relative to the patient anatomy based on the comparison received at step 680. The sonographer may also adjust the patient position. The sonographer may then acquire an additional ultrasound image. At step 670, the system 100 may again analyze the acquired ultrasound image to determine the anatomical scan window, probe orientation, and/or patient position. At step 675, the system may compare the newly determined parameters associated with the image acquired again at step 665 to the original image parameters of step 655. At step 680, the system may then display feedback based on the new comparison. In this way, a loop is created allowing a sonographer to repeatedly obtain new ultrasound images of the patient anatomy while adjusting the ultrasound probe until the scan window, probe orientation, and/or patient position match the scan window, probe orientation, and/or patient position of the previous imaging procedure retrieved at step 655.

At step 685, the method 650 includes storing the additional ultrasound image with its associated scan window and/or probe orientation. When the system 100 indicates that the scan window, probe orientation, and/or in some embodiments patient position match the same parameters of the previous ultrasound image, the new image may be stored along with the scan window, probe orientation, and/or patient position. This new image and its associated parameters may be stored in the same location as the previous image and parameters or may be stored in a different location. The new image and associated parameters may be stored in such a way that they may be retrieved at a subsequent imaging procedure. At the subsequent imaging procedure, the new image and parameters may determine the desired values to guide a sonographer to the same probe positioning. As stated with reference to FIG. 3, in some embodiments, the sonographer may have the ability to override the method 650 and store images and associated parameters even when the parameters do not match the parameters of the previous procedure. Similarly, the sonographer may direct the system 100 to revert back to step 665 of the method 650 to acquire, analyze, and compare an additional ultrasound image although all parameters associated with an image may match the previous procedure.

Figure 7:
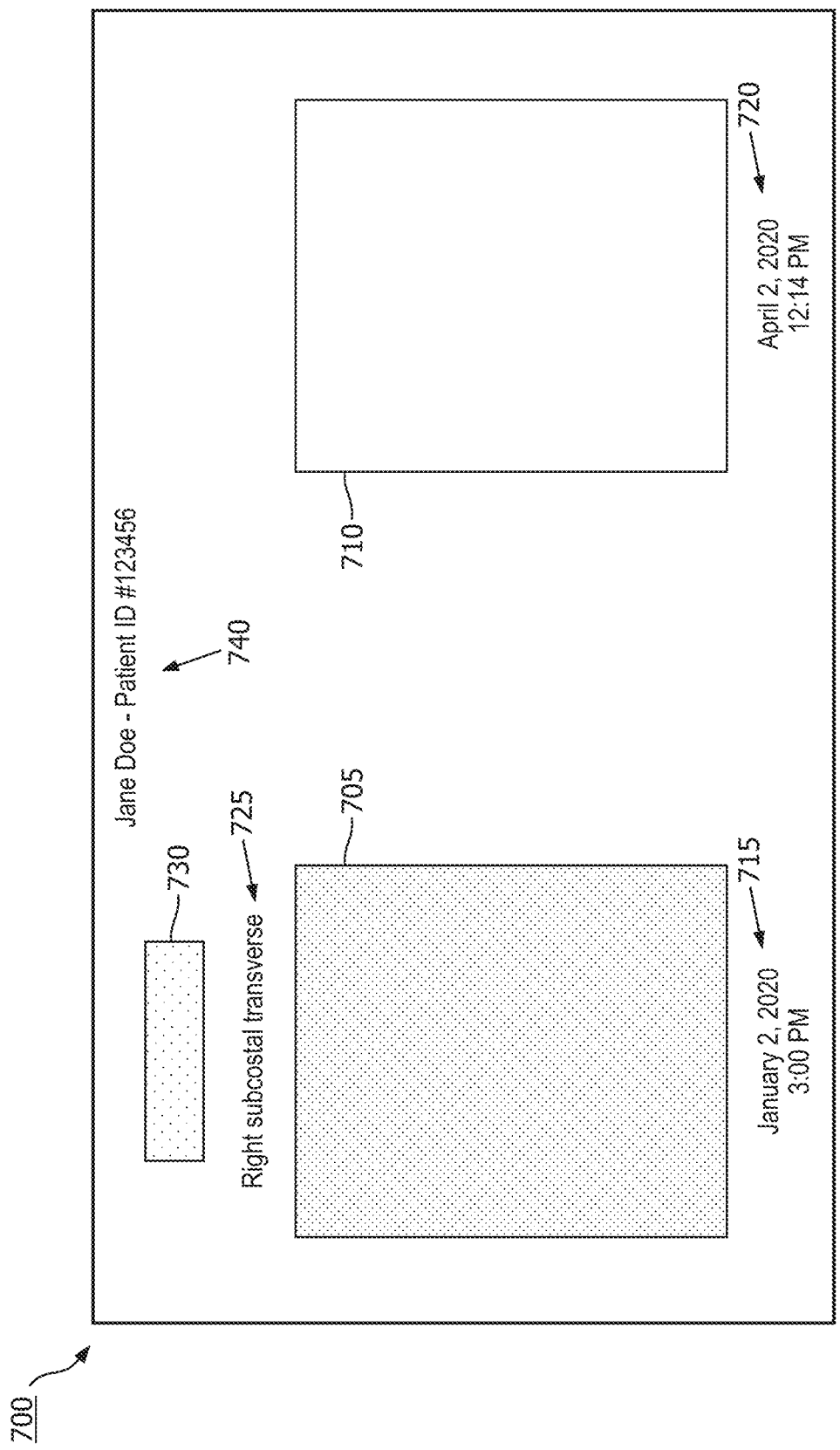
FIG. 7 is a diagrammatic view of a graphical user interface for an ultrasound imaging system comparing parameters of ultrasound images prior to acquisition of images in an additional imaging procedure, according to aspects of the present disclosure.

FIG. 7 is a diagrammatic view of a graphical user interface 700 for an ultrasound imaging system comparing parameters of ultrasound images prior to acquisition of images in an additional imaging procedure, according to aspects of the present disclosure. Referring to step 660 of the method 650 in FIG. 6, the interface shown in FIG. 7 may correspond to an exemplary user interface displayed to a user of the system 100 at step 660 in which an anatomical scan window and/or probe orientation of a previous imaging procedure may be displayed. The interface 700 includes an ultrasound image 705, biographical data 715, text 725, patient position representation 730, box 710, biographical data 720, and a title 740.

The ultrasound image 705 may be an ultrasound image acquired at a previous imaging procedure. The image 705 may depict the region of interest to be imaged at the present procedure. The image 705 may correspond to an anatomical scan window and/or probe orientation which may be used as target parameters for the present procedure. In some embodiments, the image 705 may not be displayed within the interface 700. The image 705 may be annotated with the scan window and/or probe orientation associated with the image 705, or may additionally be annotated with any other data, metric, notes, or other information.

The biographical data 715 shown beneath the ultrasound image 705 may indicate data relating to the image 705, the parameters associated with the image 705, such as an anatomical scan window and/or probe orientation, or may indicate any other data related to the imaging procedure at which the image 705 and/or associated parameters were acquired. For example, as shown, the biographical data 715 may indicate the date of the imaging procedure or the date that the image 705 was acquired. It may also indicate the time at which the image 705 was acquired. The biographical data 715 may include additional information such as, but no limited, the equipment used to obtain the image 705 and associated parameters, the physician or sonographer who performed the imaging procedure, any notes related to the imaging procedure, or any other suitable information. The biographical data 715 may be located at any suitable location within the user interface 700 including any location relative to the image 705.

Text 725 located above the ultrasound image 705 may convey to a user the parameters associated with the ultrasound image 705. For example, as shown, the text 725 may indicate the anatomical scan window and/or probe orientation corresponding to the image 705. The text 725 may additionally include information relating to other parameters, such as patient position. As noted, the text 725 may also include various continuous variable coordinates indicating probe position in addition to or in place of the probe position text. Similar to the biographical data 715, the text 725 may be located at any suitable location within the user interface 700 including any location relative to the image 705.

The patient position representation 730 shown above the text 725 may also indicate to a user the patient position of the patient at the time the image 705 was acquired. The position representation 730 may be any suitable indicator including symbols, alpha-numeric text, or images. In some embodiments, a generic image of a model patient may be displayed in the position that the actual patient was in at the time of imaging. In some embodiments, the representation 730 may be an optical camera image of the actual patient at the time of the imaging procedure. Text indicating the patient position may accompany the representation 730 or may not.

The box 710 shown adjacent to the image 705 may be a reserved space within the interface 700 for an ultrasound image from the current imaging procedure. However, as noted, the interface 700 may correspond to a time before any new ultrasound data or images have been acquired so no current ultrasound image may be available.

In the context of the user interface 700, the biographical data 720 may indicate to a user the current date and time. This data may be updated upon receipt of an additional ultrasound image acquired during the present imaging procedure. In some embodiments, the graphical user interface 700 may not include biographical information 720. Biographical information 720 may include any of the information described with reference to biographical information 715 but corresponding to the present imaging procedure as opposed to the imaging procedure associated with image 705.

Title 740 may convey additional clarifying information to a user of the system 100. For example, the title 740 may include the patient's name along with a patient identification number. In some embodiments, the title 740 may include additional information such as a patient's date of birth, age, or other information. In addition, the title 740 may include physiological information of the patient including the patient's height, weight, heart rate, respiratory rate, medical conditions, allergies, or any other suitable information relating to the patient to be imaged.

Figure 8:
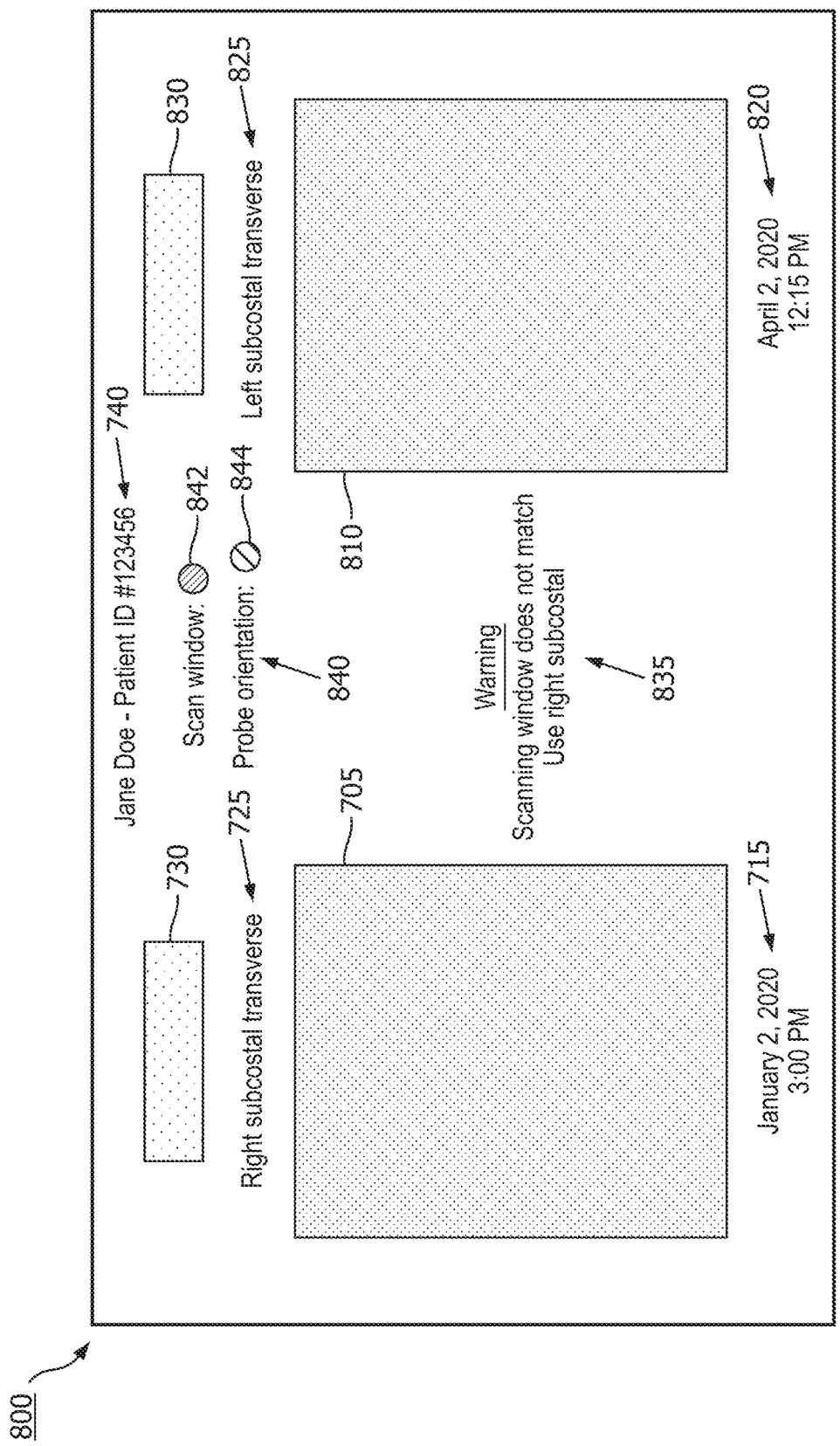
FIG. 8 is a diagrammatic view of a graphical user interface for an ultrasound imaging system comparing parameters of ultrasound images and indicating differences between the parameters, according to aspects of the present disclosure.

FIG. 8 is a diagrammatic view of a graphical user interface 800 for an ultrasound imaging system comparing parameters of ultrasound images and indicating differences between the parameters, according to aspects of the present disclosure. Graphical user interface 800 may reflect an exemplary interface displayed to a user of the ultrasound system 100 after an ultrasound image has been acquired during the present imaging procedure. Shown in FIG. 8 is the same image 705 shown in interface 700 (FIG. 7) along with the same biographical information 715, text 725, patient position representation 730, and title 740 shown and described previously. However, FIG. 8 also depicts a new ultrasound image 810, updated biographical information 820, text 825, patient position representation 830, text 835, comparison information 840, and indicators 842 and 844.

The new ultrasound image 810 may be one or more ultrasound images acquired during the present ultrasound imaging procedure (e.g., one or more image frames of an ultrasound image stream). After viewing user interface 700 for the anatomical scan window and/or probe orientation of the previous imaging procedure, the sonographer may attempt the ultrasound probe in a similar position to obtain an image with the same scan window and/or probe orientation as the previous image 705. The image 810 may be displayed to a user in the space of interface 800 previously occupied by the box 710 shown in FIG. 7. Once a sonographer is satisfied with the positioning of the ultrasound probe, they may indicate to the system 100 to record ultrasound image 810. In some embodiments, the processor circuit compares the scan window and/or probe orientation of the current ultrasound image stream to the scan window and/or probe orientation of the previous ultrasound image, as the current image stream is continuously obtained. In some embodiments, the processor circuit compares the scan window and/or probe orientation of only the recorded ultrasound image(s) from the current image stream to the scan window and/or probe orientation of the previous ultrasound image.

After acquiring and/or recording the image 810 the system 100 may replace the biographical information 720 of FIG. 7 with the updated biographical information 820. The updated biographical information 820 may reflect the date and time at which the image 810 was acquired by the system 100. If necessary, the system 100 may also update any other information of the updated biographical information 820.

Also after acquiring and/or recording the image 810, as has been described with reference to method 300 of FIG. 3 and methods 600 and 650 of FIG. 6, the system 100 may perform an analysis of the image 810 to determine the anatomical scan window and/or probe orientation associated with the image 810, as well as any other parameters. Text 825 may indicate to the sonographer the scan window and/or probe orientation of the image 810. Similar to the text 725 previously described, the text 825 may contain any suitable information and be located at any suitable location within the interface 800.

The patient position representation 830 may indicate to a user the position of the patient at the time the image 810 was acquired. Similar to the patient position representation 730, the representation 830 may be any suitable indicator, including an optical image of the patient, and may or may not be accompanied by additional text describing the patient position. It may also be positioned at any suitable location within the interface 800.

After the image 810 is acquired and displayed to the user and after the anatomical scan window and/or probe orientation as well as any other parameters are automatically determined by the system 100, the system 100 compares the scan window and/or probe orientation of the image 705 with the scan window and/or probe orientation of the newly acquired image 810. The results of the comparison may be displayed with the comparison information 840. The comparison information 840 may include any suitable type of communication including audio, visual, or other representations, including alpha-numeric text, symbols, images, or any other means of communications. In the embodiment in shown in FIG. 8, the comparison information 840 may include text relating to each parameter compared. For example, the comparison information 840 may include text related to the scan window and/or text related to the probe orientation. In some embodiments, it may also include information related to the patient position.

Each parameter compared may be accompanied by an indicator. For example, as shown the text "scan window" are accompanied by the indicator 842 and the text "probe orientation" are accompanied by the indicator 844. Text corresponding to a patient position would also be accompanied by a similar indicator.

In the example shown in FIG. 8, an indicator 842 may indicate that the associated parameter of the image 705 and the image 810 do not match. This difference is also shown by the difference in text 725 and text 825. Specifically, the anatomical scan window of the image 705 and the anatomical scan window of the image 810 are not the same. The scan window of the image 705 is right subcostal and the scan window of the image 810 is left subcostal. An indicator 844 may indicate that the associated parameter of the image 705 and the image 810 do match. This matching of parameters is shown by the same term "transverse" in text 725 and text 825. Specifically, the probe orientation of the image 705 and the probe orientation of the image 810 are both transverse. Naturally, any scan window or probe orientation may be indicated by text 725 and 825 and may produce varying results in the comparison information 840.

Text 835 may serve as an additional or alternative means of conveying the comparison results of the parameters associated with the image 705 and the image 810. In the example shown in FIG. 8, the text 835 may provide information relating to the difference in anatomical scan windows between the image 705 and 810. In some embodiments, if a parameter differs between the images, a warning may be displayed as text 835. In some embodiments, the text 835 may only convey information relating to parameters which differ. In other embodiments, the text 835 may convey information relating to all parameters whether or not they differ between images 705 and 810 or are the same.

Figure 9:
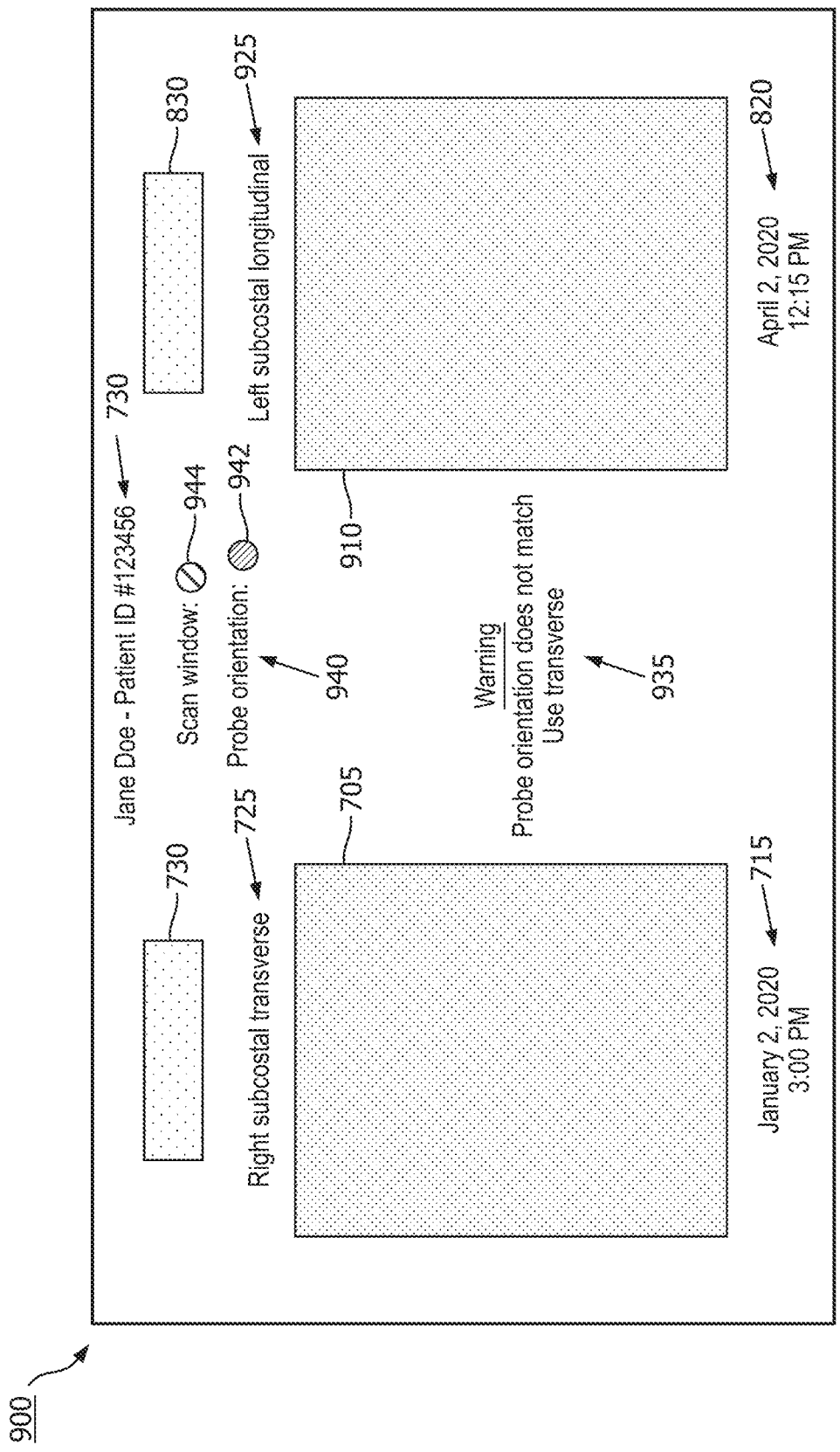
FIG. 9 is a diagrammatic view of a graphical user interface for an ultrasound imaging system comparing parameters of ultrasound images and indicating differences between the parameters, according to aspects of the present disclosure.

FIG. 9 is a diagrammatic view of a graphical user interface for an ultrasound imaging system comparing parameters of ultrasound images and indicating differences between the parameters, according to aspects of the present disclosure. Graphical user interface 900 may reflect an exemplary interface displayed to a user of the ultrasound system 100 after an ultrasound image has been acquired during the present imaging procedure, similar to graphical user interface 800. Shown in FIG. 9 is the same image 705 shown in interface 700 (FIG. 7) along with the same biographical information 715, text 725, patient position representation 730, title 740, updated biographical information 820, and patient position representation 830. However, FIG. 9 also depicts a newly acquired image 910, text 925, comparison information 940, indicators 942 and 944, and text 935.

Similar to the image 810 of FIG. 8, the new ultrasound image 910 may be an ultrasound image acquired during the present ultrasound imaging procedure. A user of the system 100 may acquire a new image 910 based on the anatomical scan window and/or probe orientation of the image 705 or in response to acquiring an image with a scan window and/or probe orientation that do not match the target parameters. After acquiring the image 910, the image 910 may be displayed to a user.

After acquiring the image 910, as has been described previously, the system 100 may perform an analysis to determine the anatomical scan window and/or probe orientation associated with the image 910, as well as any other parameters. Text 925 may indicate to the sonographer the scan window and/or probe orientation of the image 910. Text 925 may share any previously mentioned characteristics of text 725 or 825.

After the image 910 is acquired and displayed to the user and the anatomical scan window and/or probe orientation are determined, the system 100 compares the scan window and/or probe orientation of the image 705 with the scan window and/or probe orientation of the newly acquired image 910. The results of the comparison may be displayed with the comparison information 940. The comparison information 940 may be similar to comparison information 840 and may include any suitable type of communication including audio, visual, or other representations. For example, the comparison information 940 may include text related to the scan window and text related to the probe orientation. It may also include information related to the patient position.

In the example shown in FIG. 9, an indicator 942 may indicate that the associated parameter of the image 705 and the image 910 do not match. This difference is also shown by the difference in text 725 and text 925. Specifically, the probe orientation of the image 705 and the probe orientation of the image 910 are not the same. The probe orientation of the image 705 is transverse and the probe orientation of the image 910 is longitudinal. An indicator 944 may indicate that the associated parameter of the image 705 and the image 910 match. This matching of parameters is shown by the same terms "right subcostal" in text 725 and text 925. Specifically, the anatomical scan window of the image 705 and the anatomical scan window of the image 810 are both transverse.

Text 935 may serve as an additional or alternative means of conveying the comparison results of the parameters associated with the image 705 and the image 910. In the example shown in FIG. 9, the text 935 may provide information relating to the difference in probe orientation between the image 705 and 910.

Figure 10:
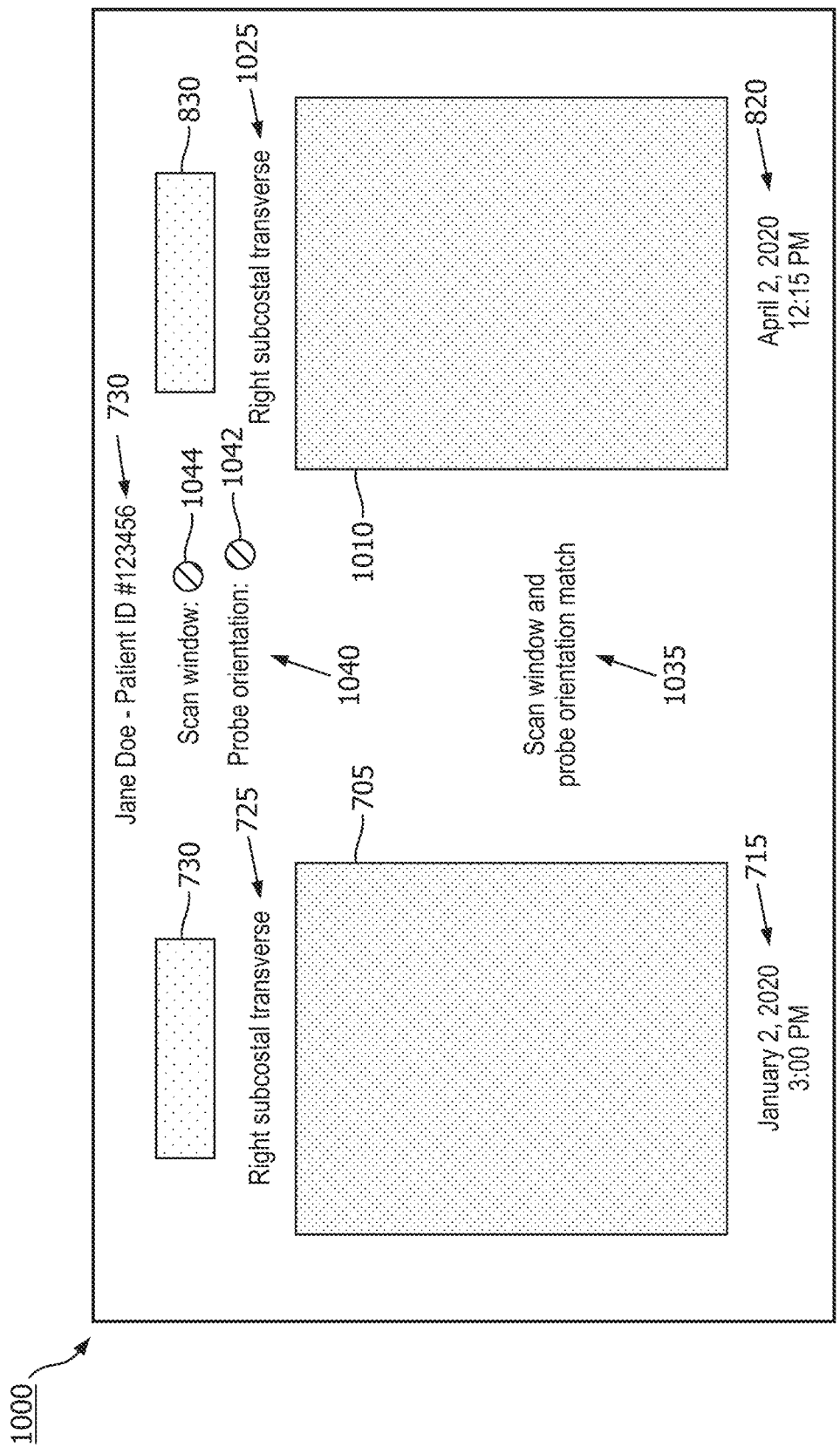
FIG. 10 is a diagrammatic view of a graphical user interface for an ultrasound imaging system comparing parameters of ultrasound images and indicating the parameters are the same, according to aspects of the present disclosure.

FIG. 10 is a diagrammatic view of a graphical user interface for an ultrasound imaging system comparing parameters of ultrasound images and indicating the parameters are the same, according to aspects of the present disclosure. Graphical user interface 1000 may reflect an exemplary interface displayed to a user of the ultrasound system 100 after an ultrasound image has been acquired during the present imaging procedure, similar to graphical user interfaces 800 and/or 900. Shown in FIG. 10 depicts many similar elements as FIG. 8 and/or FIG. 9. However, FIG. 10 depicts a newly acquired image 1010, text 1025, comparison information 1040, indicators 1042 and 1044, and text 1035.

Similar to the image 810 of FIG. 8 and 910 of FIG. 9, the new ultrasound image 1010 may be an ultrasound image acquired during the present ultrasound imaging procedure. A user of the system 100 may acquire a new image 1010 based on the anatomical scan window and/or probe orientation of the image 705 or in response to acquiring an image with a scan window and/or probe orientation that do not match the target parameters. After acquiring the image 1010, the image 1010 may be displayed to a user.

After acquiring the image 1010, as has been described previously, the system 100 may perform an analysis to determine the anatomical scan window and/or probe orientation associated with the image 1010, as well as any other parameters. Text 1025 may indicate to the sonographer the scan window and/or probe orientation of the image 1010.

Text 1025 may share any previously mentioned characteristics of text 725, 825, or 925.

After the image 1010 is acquired and displayed to the user and the anatomical scan window and/or probe orientation are determined, the system 100 compares the scan window and/or probe orientation of the image 705 with the scan window and/or probe orientation of the newly acquired image 1010. The results of the comparison may be displayed with the comparison information 1040. The comparison information 140 may be similar to comparison information 840 or 940 and may include any suitable type of communication including audio, visual, or other representations. For example, the comparison information 1040 may include text related to the scan window and text related to the probe orientation. It may also include information related to the patient position.

In the example shown in FIG. 10, an indicator 1044 may indicate that the associated parameter of the image 705 and the image 1010 match. Specifically, the anatomical scan window and probe orientation of the image 705 and the scan window and probe orientation of the image 1010 are both "right subcostal transverse" in text 725 and text 1025.

Text 1035 may serve as an additional or alternative means of conveying the comparison results of the parameters associated with the image 705 and the image 1010. In the example shown in FIG. 10, the text 1035 may indicate that both the anatomical scan window and probe orientation of image 705 and 1010 are the same.

In some embodiments, any of the graphical user interfaces described, including interfaces 700, 800, 900, and 1000, may depict physiological conditions such as heart rate and respiration rate, among other conditions. These physiological conditions may influence wash—in, washout phases of contrast agent within the patient body, which are used to better visualize anatomical structures. This physiological information can also be recorded by the system 100 (e.g. using the patient sensor 142 of FIG. 1) or estimated based on motion seen in imaging. These physiological conditions may also be compared with previous values and used to guide subsequent acquisition so that their impact on the results are considered and minimized. In some embodiments, physiological condition measurements may be estimated using the deep learning network previously described or may be additional inputs to the deep learning network. In other embodiments, the estimation or use of physiological condition measurements may be integrated in a different deep learning network separate from the network tasked with estimating ultrasound image parameters such as anatomical scan window and/or probe orientation. In an embodiment in which physiological conditions are estimated by a deep learning network, the network may be tasked with detecting motion to output the estimated physiological measurements.

Training the deep learning network may be accomplished with various different techniques. In one embodiment, training the deep learning network may be accomplished by creating a large dataset of sample ultrasound images of different scan windows and/or probe orientations. The sample images may additionally be obtained from a large number of patients. In an embodiment in which a deep learning network is trained to identify image parameters such as scan windows and/or probe orientations from images depicting many different regions of interest, the sample images may depict a wide variety of regions of interest. In embodiments in which multiple deep learning networks are trained, each may be tasked with identifying image parameters of ultrasound images depicting only one region of interest. In such an embodiment, a large number of sample images selected for the training of one deep learning network may all depict the same type of region of interest, though each would still depict various scan windows and/or probe orientations and be obtained from a large number of different patients.

As an example of one embodiment of training, each sample image selected for the training of a deep learning network may be assigned a variable $I_k$. Each image $I_k$ may be assigned a label $L_k$, where $L_k$ corresponds to the anatomical scan window and/or probe orientation used for image acquisition of the image $I_k$. The deep learning network may be trained batch-wise, using batches of tuples $(I_k, L_k)$, where $I_k$ is a possibly preprocessed ultrasound image, and $L_k$ is a corresponding label in the form of an ordinal $(1,2,3,\ldots)$ representing the anatomical scan window and/or probe orientation used during acquisition of image $I_k$. In some embodiments, the label of the scan window and/or probe orientation may also be separated into two separate values $[S_k, P_k]$ where $S_k$ corresponds to a scan window associated with the image $I_k$ and $P_k$ corresponds to a probe orientation associated with the image $I_k$. Training is then performed with the tuples $(I_k, [S_k, P_k])$, where $[S_k, P_k]$ includes the group of separate values describing the scan window and/or probe orientation. Additional values may be added corresponding to the patient position, or any other parameter associated with an image $I_k$. Methods of generating the label $L_k$ are described below.

For training the network, random batches of tuples $(I_k, L_k)$ may be generated. The images may be forward-propagated through the deep learning network, creating a tentative label assignment $L_k'$ for each image. A loss function may be defined to measure the size of the error between $L_k$ and $L_k'$ for all labels in the batch. The error may then be back-propagated through the network and an optimizer is used to adjust the network's parameters in order to improve subsequent predictions. The training process may continue for a fixed number of iterations or until some convergence criterion is met. For example, the training process may continue until the error no longer improves for a specified number of iterations.

In one embodiment, the loss function used during the training of the deep learning network may measure whether the estimated angle of the probe and/or anatomical scan window of the probe is correct or incorrect. For example, given a finite set of labels that the deep learning network may be trained to identify, the network may assign probabilities for each of the classes. For instance, the network may assign a probability of 80% for one class and 1% for another classes. The loss function may then determine an error metric indicating how well the network predicts with high likelihood the correct label and low likelihood the incorrect labels. The loss function may include various other features or steps. For example, in an embodiment in which the probe orientation is defined as various three-value coordinates as opposed to a finite set of labels, the loss function may include an error metric relating to the difference in degrees or radians between the predicted angle of the probe in any of the defined axes and the actual angle of the probe.

Figure 11A:
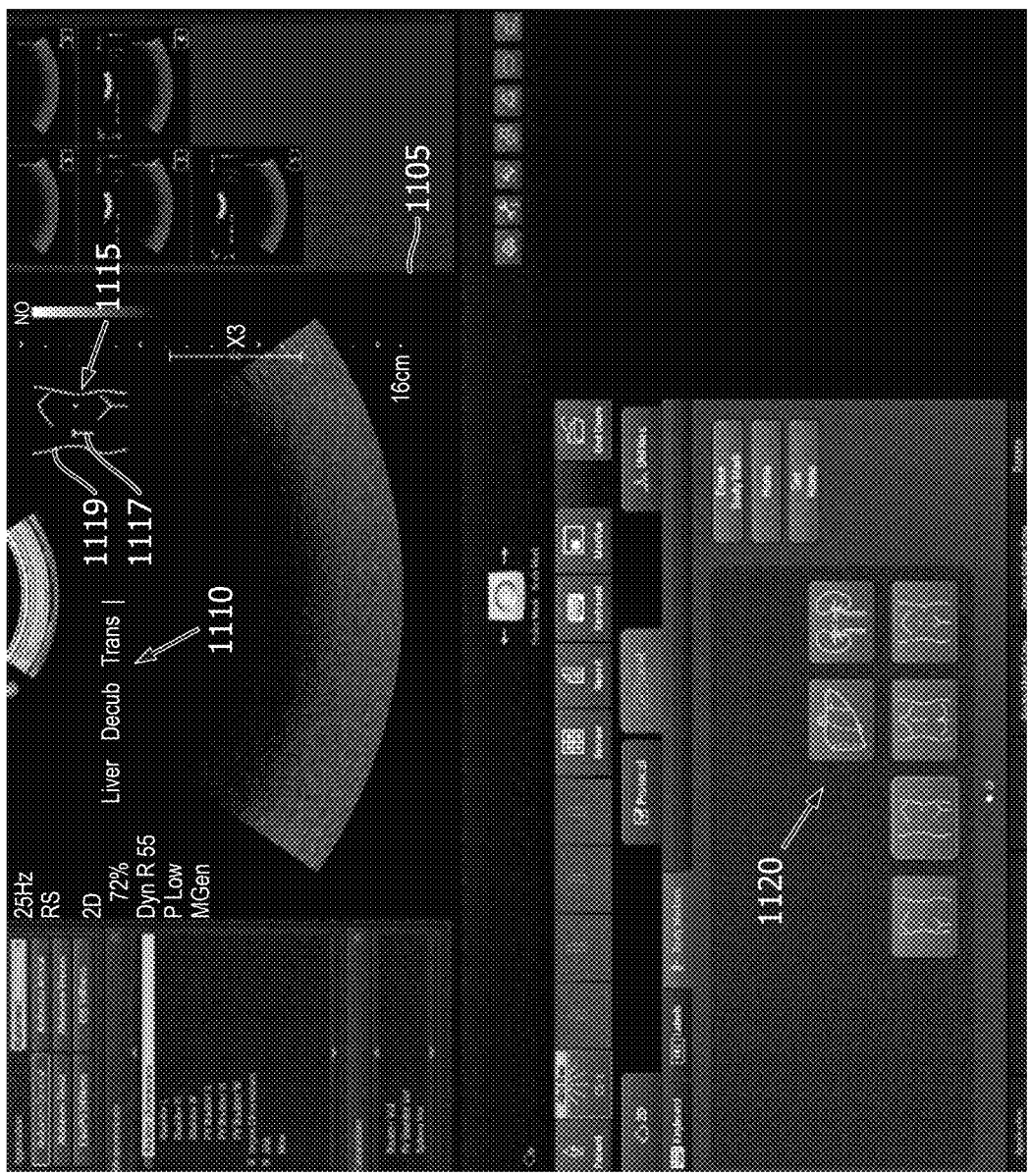
FIG. 11A is a diagrammatic view of a graphical user interface for annotating ultrasound images at a training stage of a deep learning network, according to aspects of the present disclosure.

One method for obtaining the labels $L_k$ is by having expert sonographers assign the label $L_k$ at the time of image acquisition (prospectively) or at the time of image review (retrospectively). Such a method is described in more detail with reference to FIG. 11A and FIG. 11B. FIG. 11A is a diagrammatic view of a graphical user interface 1100 for annotating ultrasound images at a training stage of a deep learning network, according to aspects of the present disclosure. Users, such as experts in the field, tasked with annotating ultrasound images selected within a training set of sample ultrasound images may view and use an interface similar to interface 1100 to assign labels to each image. Graphical user interface 1100 depicts an ultrasound image 1105, text 1110, graphic 1115 including a model 1119 and an indicator 1117, and selections 1120.

The ultrasound image 1105 may be obtained using the ultrasound system 100 or any other similar ultrasound system. The image 1105 may depict any suitable region of interest. An expert sonographer may indicate to the system 100 to retrieve the ultrasound image 1105 for display. The expert sonographer may select from a variety of selections 1120 corresponding to aspects of the image 1105. For example, the sonographer may indicate the region of interest shown in the ultrasound image 1105 and/or the position of the patient relative to the ultrasound imaging probe, among other parameters of the ultrasound image. As the sonographer identifies parameters from the available selections 1120, data corresponding to the ultrasound image 1105 may be updated. For example, as shown in FIG. 11A, after an expert sonographer selects the patient positions highlighted among the selections 1120, the graphic 1115 may reflect the decision.

The graphic 1115 may serve as an indication of an expert sonographer's chosen selections 1120. It may include any suitable visual representation including alpha-numeric text, symbols, models, and/or images. In the embodiment shown in FIG. 11A, the graphic 1115 depicts a model 1119. The model 1119 may reflect the sonographer's choice of the selections 1120 and may indicate the patient position at the time the ultrasound image 1105 was acquired. The graphic 1115 may additionally include the indicator 1117. The indicator 1117 may illustrate any suitable information relating to the labelling of the image 1105. In some embodiments, the indicator 1117 may illustrate the estimated location of the ultrasound probe relative to the patient's body at the time the image 1105 was acquired. Any suitable number or type of indicators may be included within the graphic 1115 as well conveying any suitable information relating to the image 1105.

Text 1110 shown overlaid over the acquired ultrasound image 1105 along with the graphic 1115 may also convey to a user of the system 100 the current parameters selected by the expert. For example, the text 1110 may indicate the type of region of interest the expert has indicated that the ultrasound image 1105 depicts. The text 1110 may also depict any other suitable information, such as the anatomical scan window and/or probe orientation selected by the expert user at the time, or other information related to the ultrasound image 1105.

It is noted that although the graphic 1115 and text 1110 are shown in the interface 1100 of FIG. 11 as positioned overlaid on the image 1105, the graphic 1115 and text 1110 may be positioned in any suitable location within the interface 1100 in relation to the image 1105. Similarly, although the selections 1120 are shown beneath the image 1105, they may also be positioned in any suitable location within the interface 1100.

Figure 11B:
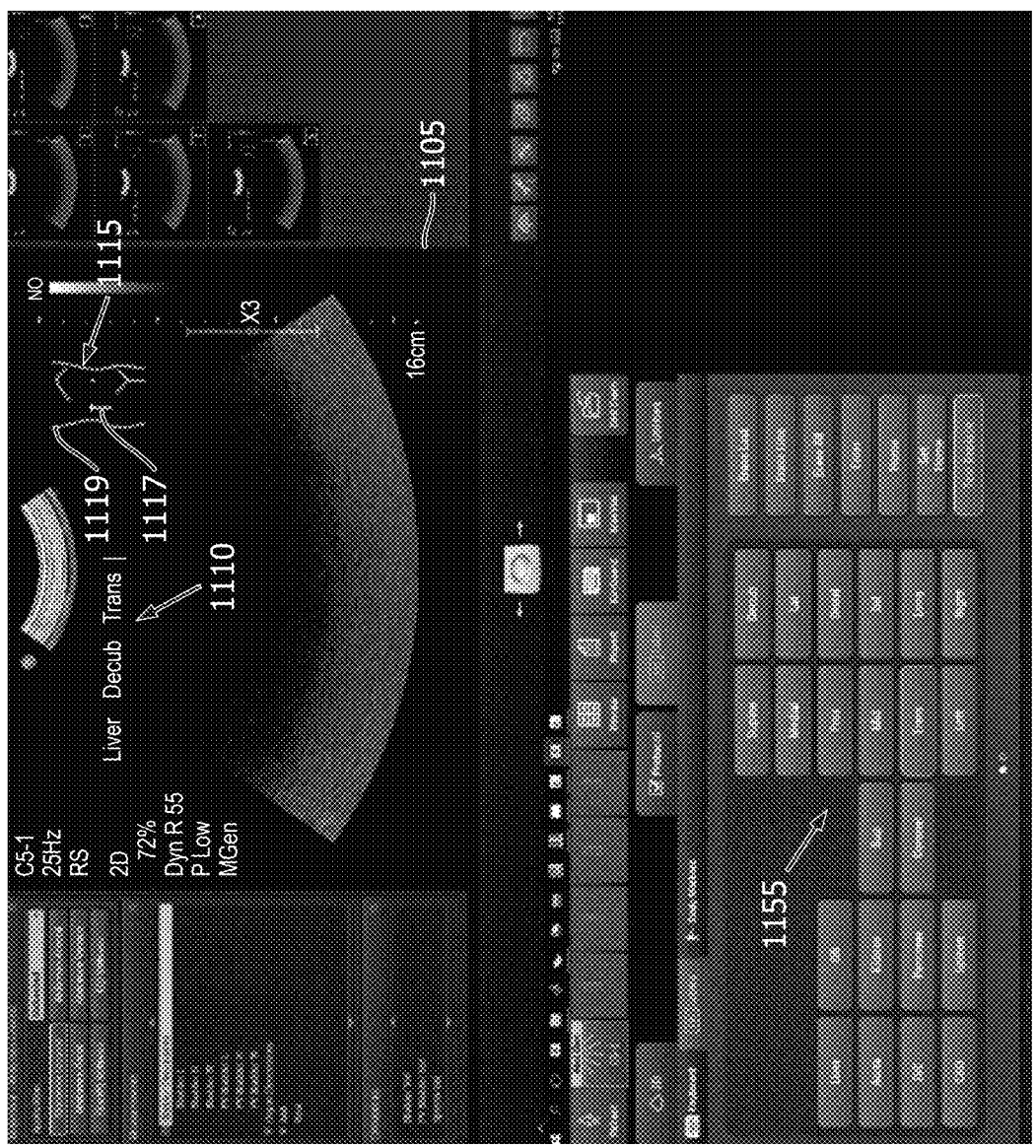
FIG. 11B is a diagrammatic view of a graphical user interface for annotating ultrasound images at a training stage of a deep learning network, according to aspects of the present disclosure.

FIG. 11B is a diagrammatic view of a graphical user interface 1150 for annotating ultrasound images at a training stage of a deep learning network, according to aspects of the present disclosure. FIG. 11B may be a separate interface from interface 1100 described with reference to FIG. 11A. Graphical user interface 1150 may also be an alternate or additional view of the same interface 1100. Graphical user interface 1150 depicts additional or alternative selections 1155 available to an expert sonographer tasked with creating labels for the ultrasound image 1105 shown.

The selections 1155 may be of any suitable type. In some embodiments, selections 1155 may be alternative selections to the selections 1120 available to an expert sonographer shown in FIG. 11A. In some embodiments, selections 1120 and/or selections 1155 may be selectable buttons within a user interface. In some embodiments, an expert sonographer may enter text reflecting any of the image parameters such as anatomical scan window, probe orientation, patient position, and/or others. The selections 1155 shown in FIG. 11B may be buttons containing text. The selections may also contain images or symbols similar to the selections 1120 shown in FIG. 11A. Similar to the graphical user interface 1100, experts in the field tasked with annotating ultrasound images may view and use an interface similar to interface 1150 to assign labels to each image.

Other methods of automatically providing a label $L_k$ for an image $I_k$ can be implemented using a tracking system. The tracking system can be an optical tracking system in some embodiments. Optical camera tracking may involve a photographic device used in conjunction with the ultrasound imaging system. For example, an optical camera can obtain images of the patient and the probe during image acquisition. The optical images depict the probe location on the patient's body and body positioning of the patient. Based on the probe location and body positioning, the processor circuit can determine the labels $L_k$ for anatomical scan window and/or probe orientation. For example, using image processing techniques, a processor circuit may identify the head and feet of patient as well as the left and right regions of the patient to create a coordinate system of the patient. The processor may then use similar image processing techniques to identify the coordinate system of the probe. The processor circuit may then compare the two coordinate systems to identify the probe orientation. In some embodiments, the system 100 may also identify various features within the image received from the photographic device to determine a scan window. In such an embodiment, the system 100 may use image processing techniques to identify the location of ribs or bones within the patient anatomy and determine the location and direction of the probe 1222 in relation to those ribs or other bones.

Figure 12:
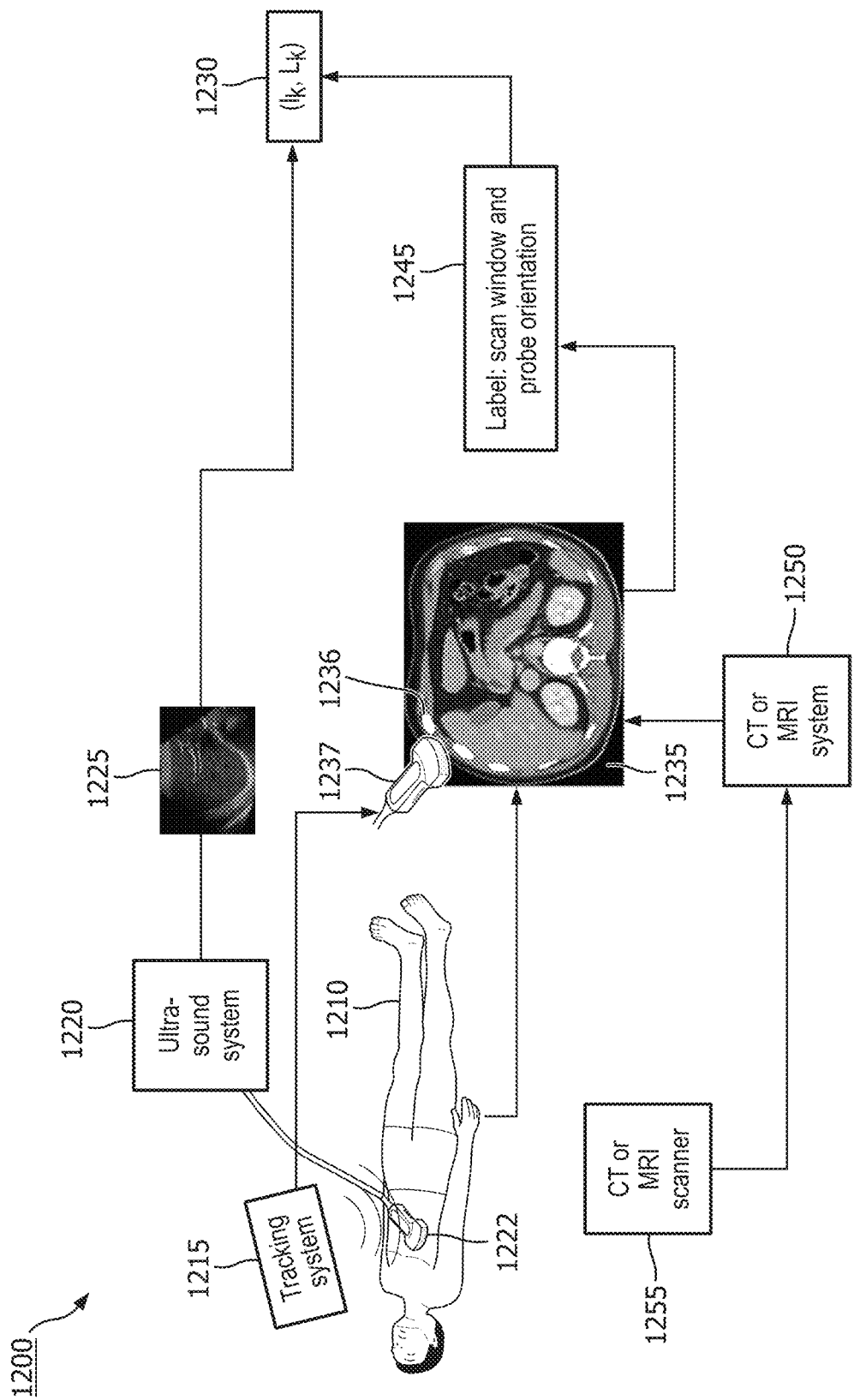
FIG. 12 is a diagrammatic view of a computed tomography and ultrasound system for automatically annotating images at a training stage of a deep learning network, according to aspects of the present disclosure.

In other embodiments, an electromagnetic tracking may be used along with two imaging modalities (e.g., ultrasound and CT, or ultrasound and MRI) to automatically provide a label $L_k$ for an image $I_k$, as will be described with more detail with reference to FIG. 12. FIG. 12 is a diagrammatic view of a computed tomography (CT) or magnetic resonance imaging (MRI) and ultrasound system 1200 for automatically annotating images at a training stage of a deep learning network, according to aspects of the present disclosure. For example, the system 1200 can automatically assign the labels $L_k$ for anatomical scan window and/or probe orientation. The system 1200 may be similar to the Philips® PercuNav® system. The system 1200 may be referenced as a fusion imaging system in that it combines image data from two different imaging modalities (ultrasound and CT/MRI).

FIG. 12 depicts a patient 1210, ultrasound system 1220 including an ultrasound probe 1222, a CT or MRI system 1250 including a CT or MRI scanner 1255, and a tracking system 1215. The ultrasound system 1220 and/or the probe 1222 may be similar to the ultrasound system 100 and/or the probe 110 described herein. FIG. 12 also illustrates ultrasound image 1225 of the patient 1210 generated by the ultrasound system 1220 based on ultrasound data acquired by the probe 1222, as well as the image 1235 of the patient 1210 generated by the CT/MRI system 1250 generated based on CT or MRI data acquired by the CT/MRI scanner 1255. Also shown in FIG. 12 is a label 1245 automatically generated based on the image 1235, and an image and label pair (or tuple) 1230. The image 1235 may be a CT image or an MRI image. The image 1235 may be a 3D image, although only a 2-dimensional axial cross-section is shown for simplicity. In other embodiments, the image 1235 may also be a 2D image and can be taken along the coronal plane of the patient 1210 or along any other suitable plane. The system 1250 shown may be a CT system or an MRI system. Similarly, the scanner 1255 may be a CT scanner or an MRI scanner. Features of both CT and MRI imaging systems may be implemented in the present disclosure to obtain the image 1235. The image 1235 may be a CT image, an MRI image, or any other suitable image. A processor circuit automatically segments the image 1235 to identify structures 1236 within the patient body, such as the patient's ribs. The sonographer may place the ultrasound probe 1222 at a suitable location on or near the anatomy of the patient 1210. The ultrasound system 1220 controls the probe 1222 to acquire the ultrasound image 125, which itself can be the image $I_k$ of the tuple 1230.

The tracking system 1215 can be an electromagnetic tracking system that tracks the ultrasound probe 1222 based on the strength of a magnetic field. The tracking system 1215 registers and tracks the pose (e.g., position and/or orientation) of an ultrasound probe 1222 and an ultrasound image 1225 generated by the ultrasound system 1220, relative to a 3D image (such as the CT or MRI image 1235). The ultrasound system 1220 can spatially co-register the image 1235, and the ultrasound image 1225 by analyzing (e.g., performing image processing on) the CT/MRI image 1235 and the ultrasound image 1225 and automatically matching the same structures (e.g., ribs) within the images. The system 1200 can include aspects similar to those described in U.S. Pat. No. 10,290,076, titled "System and method for automated initialization and registration of navigation system," and granted May 14, 2020, which is hereby incorporated by reference in its entirety.

Probe tracking with the electromagnetic tracking system 1215 allows for the position and orientation of the probe relative to a CT or MRI image of the patient to be identified. This probe orientation relative to the patient's CT or MRI image forms part of the label 1245. Probe position (tracked by the electromagnetic tracking system 1215) relative to the structure (e.g., rib, bone) segmentation in the images allows for identification of the scan window because of the spatial co-registration between the image 1235 and the ultrasound image 1225. For example, a tracked probe position in a location inferior to the segmented rib cage would be identified as a subcostal window, and a probe position on the right side of the rib cage would be identified as a right scan window. This scan window forms part of the label 1245. Illustration 1237 representing the determined position and orientation of the probe relative to the patient body 1210 is provided at the corresponding location in the image 1235. The label 1245 is the label $L_k$ of the tuple 1230. The tuple 1230 may be generated for each ultrasound image within a training set. Each tuple 1230 may include the ultrasound image 1225 (e.g., image $I_k$), and the label 1245 (e.g., label $L_k$) associated with a scan window and/or probe orientation, as well as any other value corresponding to other parameters of the image (e.g., patient position).

Figure 13:
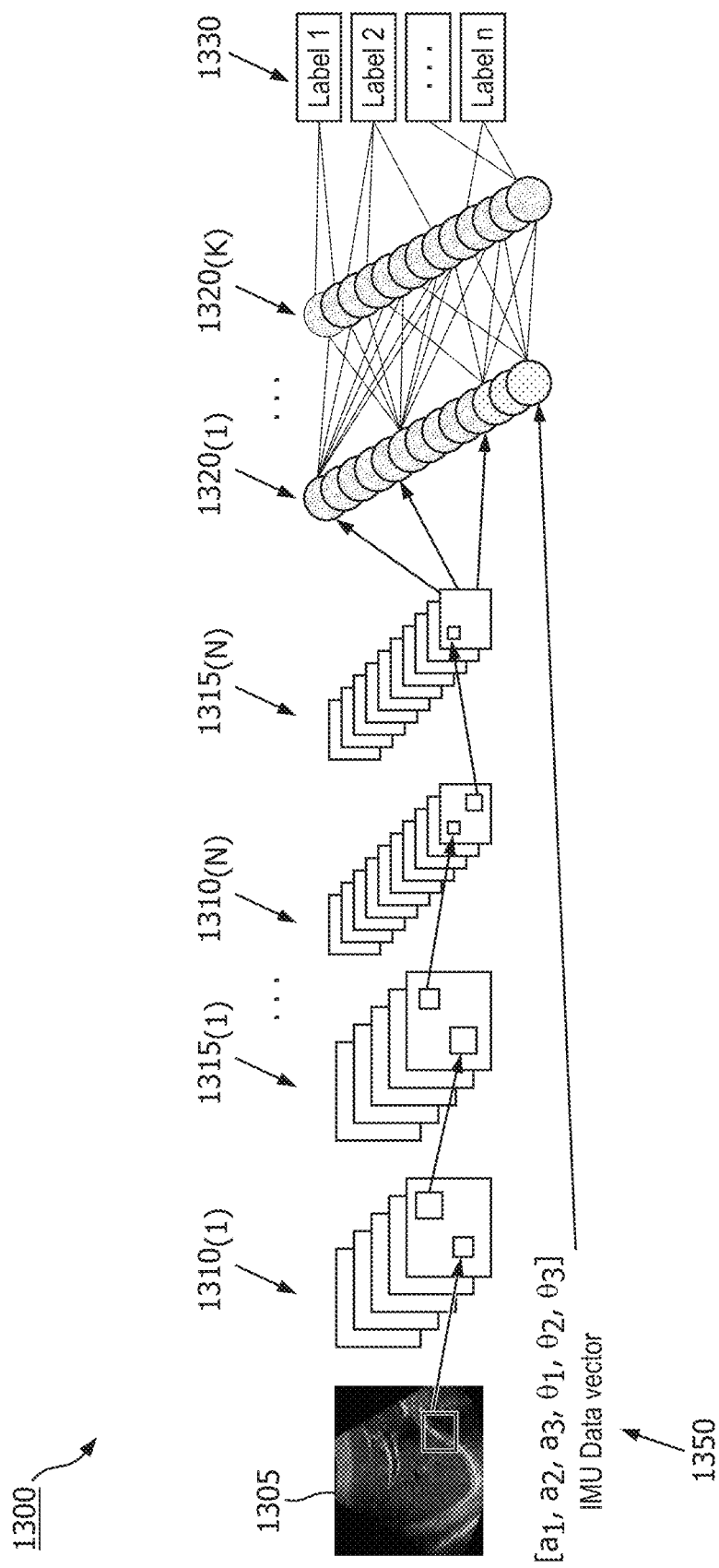
FIG. 13 is a schematic diagram of a CNN configuration including inertial measurement unit (IMU) data, according to aspects of the present disclosure.

FIG. 13 is a schematic diagram of a CNN configuration 1300 including inertial measurement unit (IMU) data, according to aspects of the present disclosure. The CNN configuration 1300 may be similar to the configuration 500 described with reference to FIG. 5.

The input of the configuration 1300 may be an ultrasound image 1305. Similar to the network configuration 500, the CNN configuration 1300 may include a number of N convolutional layers 1310, each layer being followed by a pooling layer 1315. The configuration 1300 may also include a number of fully connected layers 1320, as shown in FIG. 13. As an output, the CNN configuration 1300 may assign a label to the input image 1305 at a classification step 1330 similar to the classification output 530 of FIG. 5. Any of the layers and inputs and outputs shown in configuration 1300 may be substantially similar to the layers, inputs, and outputs of the configuration 500 described with reference to FIG. 5.

The configuration 1300 shown in FIG. 13 may receive an IMU data vector 1350 as an additional input. The IMU data vector 1350 may include orientation information ($\theta 1$, $\theta 2$, $\theta 3$) and acceleration information ($a_1$, $a_2$, $a_3$) of the ultrasound probe as two sets of three continuous variables. The IMU data vector 1350 may also contain additional information related to the position of the ultrasound probe such as rotational velocity or magnetic field components. Many ultrasound probes are equipped with IMU sensors to provide accelerometer and gyroscope data in real-time. This data may be used to determine the probe's angulation relative to gravity, and to determine relative changes in probe rotation around all three probe axes. This data can be provided in addition to the image data 1305 as input to the network 1300. The network 1300 may embed the additional data vector for example by concatenating it with the first fully connected layer $1320_{(1)}$. This additional IMU data may thus be used both at training and application/inference phases of the network 1300. Including the IMU data as an input in addition to an image 1305 can serve to improve the accuracy of the prediction. In some embodiments, IMU data may improve the estimate for probe orientation. In some embodiments, the IMU data may estimate the probe orientation over extended periods of time. As shown in FIG. 13, the output of the network 1300 may be the same as the output of the network 500 shown in FIG. 5. In some embodiments, the IMU data may be compared to the patient coordinate system as will be described with more detail with reference to FIG. 16.

Figure 14:
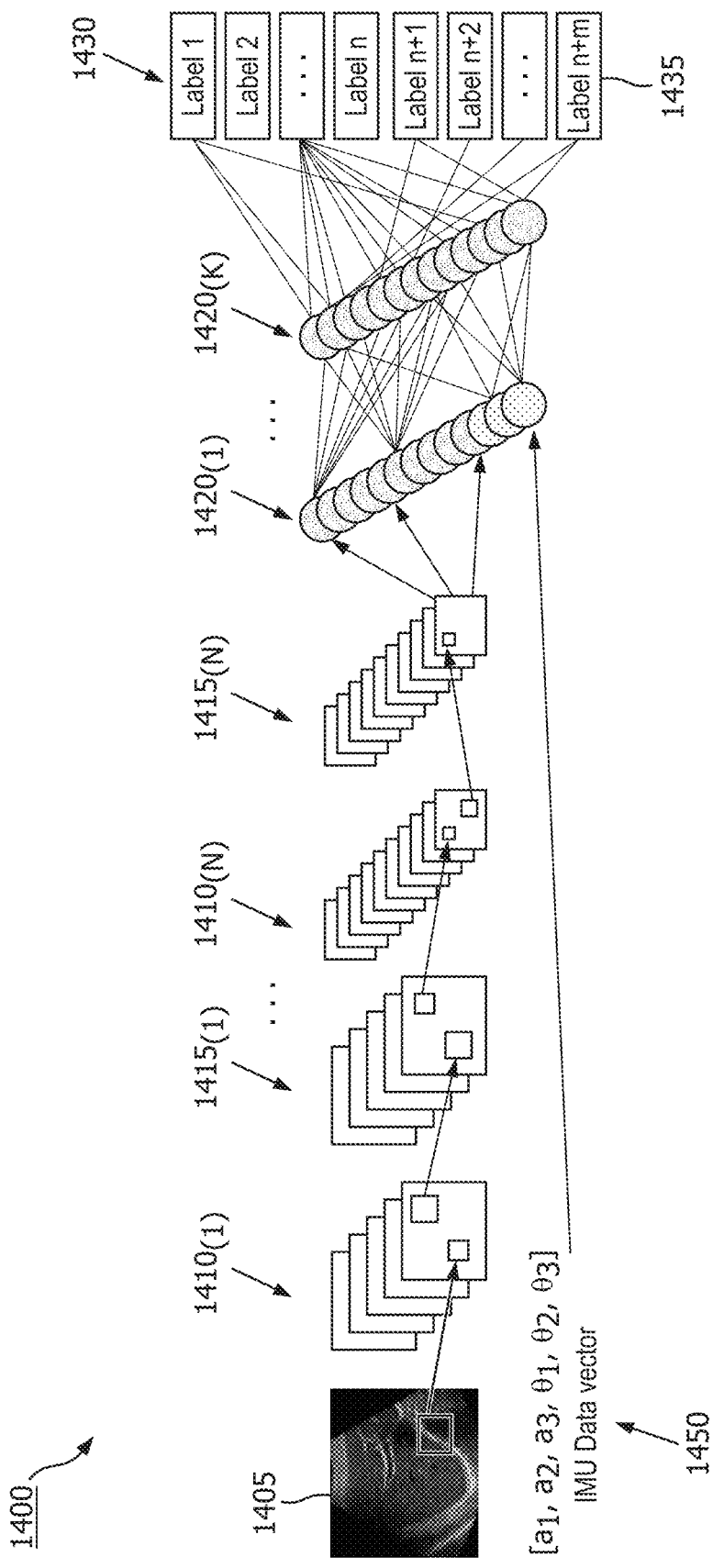
FIG. 14 is a schematic diagram of a CNN configuration including IMU data and outputting additional labels, according to aspects of the present disclosure.

FIG. 14 is a schematic diagram of a CNN configuration 1400 including IMU data, according to aspects of the present disclosure. The CNN configuration 1400 may be similar to the configuration 500 described with reference to FIG. 5 and/or the configuration 1300 described with reference to FIG. 13.

The input of the configuration 1400 may be an ultrasound image 1405. Similar to the network configurations 500 and/or 1300, the CNN configuration 1400 may include a number of K convolutional layers 1410, each layer being followed by a pooling layer 1415. The configuration 1400 may also include a number of fully connected layers 1420, as shown in FIG. 14. As an output, the CNN configuration 1400 may assign a label to the input image 1405 at a classification step 1430 similar to the classification output 530 of FIG. 5 and or 1330 of FIG. 13. Any of the layers and inputs and outputs shown in configuration 1400 may be substantially similar to the layers, inputs, and outputs of the configuration 500 described with reference to FIG. 5 or configuration 1300 of FIG. 13.

Similar to the configuration 1300 (FIG. 13), the configuration 1400 shown in FIG. 14 may receive an IMU data vector 1450 as an additional input. For example, the network

1400 may embed the additional data vector 1450 by concatenating it with the first fully connected layer 1420$_{(1)}$. The configuration 1400 additionally allows for classification of the patient position for the input image 1405 (e.g., the position that the patient was in when the image 1405 was acquired). Exemplary patient positioned are described with respect to FIG. 15. Use of IMU data to determine patient position is described with respect to FIG. 16. The labels 1435 of the classification output 1430 additionally include a patient position, as well as scan window and probe orientation (as described with respect to FIGS. 5 and 13). The classification output 1430 includes a greater quantity of labels 1435 compared to the classification outputs 530 (FIG. 5) and 1330 (FIG. 13) because the inclusion of patient position as one of the parameters generates additional parameter combinations. For example, the classification outputs 530 (FIG. 5) and 1330 (FIG. 13) include n labels (e.g., combinations of possible scan windows and probe orientations). By adding m possible patient positions while maintaining all scan window and probe orientation combinations, the classification output 1430 includes n*m labels.

Figure 15:
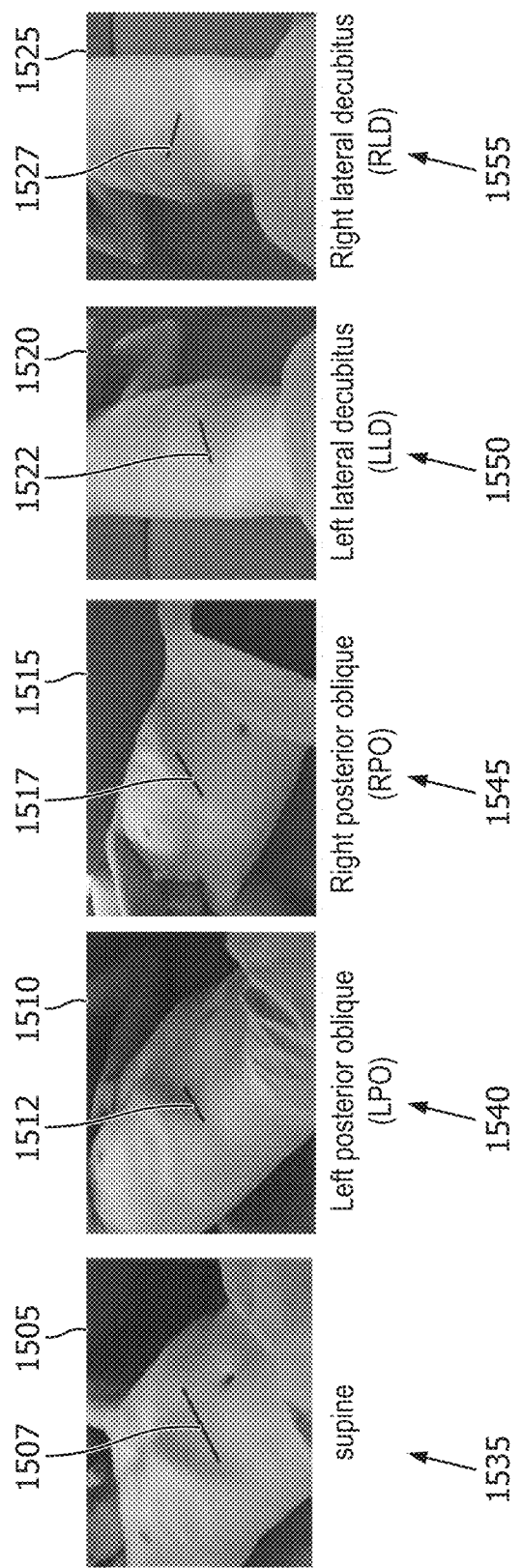
FIG. 15 is a diagrammatic view of example patient positions, according to aspects of the present disclosure.

FIG. 15 is a diagrammatic view of example patient positions, according to aspects of the present disclosure. In some applications, patient positioning may be an important parameter for reproducible longitudinal measurements. FIG. 15 depicts a number of commonly used patient poses for liver scanning, as a non-limiting example.

FIG. 15 depicts an image 1505 depicting a region of a patient in a supine position 1535. The image 1505 also depicts an indicator 1507 corresponding to the location of a scan window for viewing a region of interest, such as a liver within the patient shown. Image 1510 depicts a region of a patient in a left posterior oblique (LPO) position 1540. The image 1510 also depicts an indicator 1512 corresponding to the location of the region of interest. Image 1515 depicts a region of a patient in a right posterior oblique (RPO) position 1545. The image 1515 also depicts an indicator 1517 corresponding to the location of the region of interest. Image 1520 depicts a region of a patient in a left lateral decubitus (LLD) position 1550. The image 1520 also depicts an indicator 1522 corresponding to the location of the region of interest. Finally, image 1525 depicts a region of a patient in a left lateral decubitus (RLD) position 1555. The image 1525 also depicts an indicator 1527 corresponding to the location of the region of interest. Any of these positions shown in FIG. 15 may serve as the additional labels 1435 of FIG. 14. Additional patient positions may be available labels depending on the region of interest to be imaged, the parameters to be identified by the deep learning network, or any other characteristics.

Figure 16:
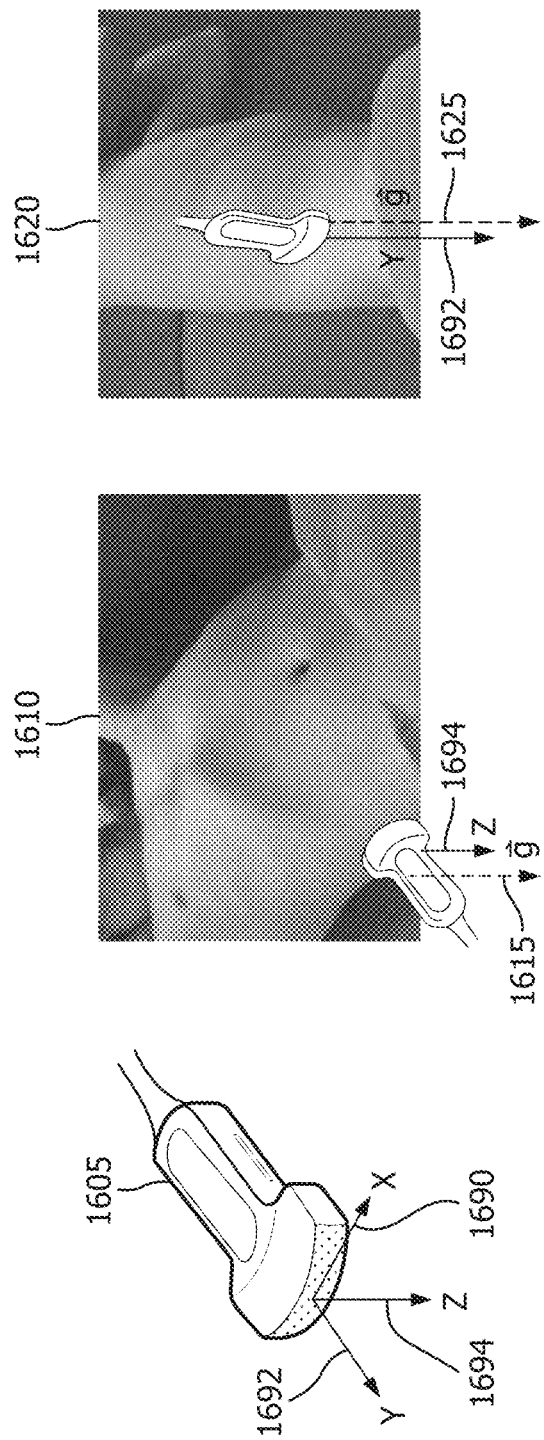
FIG. 16 is a diagrammatic view of an ultrasound probe in various orientations, according to aspects of the present disclosure.

FIG. 16 is a diagrammatic view of an ultrasound probe in various orientations, according to aspects of the present disclosure. Using IMU data measurements from the ultrasound probe, the ultrasound system 100 may determine the patient position during an ultrasound imaging procedure. FIG. 16 shows an ultrasound transducer probe 1605 with three axes including an x-axis 1690, a y-axis 1692, and a z-axis 1694. FIG. 16 also depicts an image 1610 in conjunction with the probe 1605 and a gravity vector 1615. FIG. 16 also depicts an image 1620 in conjunction with the probe 1605 and a gravity vector 1625.

The ultrasound probe 1605 shown in FIG. 16 may be substantially similar to the probe 110 of FIG. 1, the probe 1222 of FIG. 12, or any other probe described herein. The positioning or orientation of the probe 1605 may be defined by coordinate system shown. For example, the x-axis 1690 may be defined as the directions to the left and right of the probe. The y-axis may be defined as extending directly in front of and behind the probe 1605, or in the primary direction of sound propagation. The z-axis 1694 may be defined as extending directly above and below the ultrasound probe 1605 as shown. The origin of these axes 1690, 1692, and 1694 shown in FIG. 16 may be any suitable location on or within the probe 1605. For example, in one embodiment, the origin may be defined as a midpoint along the ultrasound transducer array.

Generally, the patient may rest on a primarily horizontal surface. This horizontal surface may serve as a reference horizontal surface. Depending on the patient position, the ultrasound probe 1605 will be orientated differently relative to the reference horizontal surface as shown by the orientation of the probe in relation to the patient in the image 1610 and the image 1620. Differences in probe orientation relative to the reference horizontal surface may be identified with the IMU readings of the probe 1605. The IMU readings may then be used to learn and estimate patient positioning. For example, if a lateral view is obtained with the patient in supine position as shown in the image 1610, the IMU reading of the probe 1605 would measure that the gravitational acceleration (i.e. the "down" direction) as shown by the gravitational vector 1615 is aligned with the probe's z-axis 1694. However, if the same scan plane is obtained with the patient in left lateral decubitus position as shown in the image 1620, the gravitational acceleration as shown by the gravitational vector 1625 is aligned with the probe's y-axis 1692. A modified network can thus be trained to predict—based on corresponding image and IMU data input—both the anatomical scan window and probe orientation as well as the patient positioning as output using an extended set of labels 1435 described with reference to FIG. 14, or a second but similar network can be trained to classify the patient positioning only. In this way, the ultrasound system 100 may use the combination of IMU data and patient orientation as shown in a captured image to estimate probe orientation and IMU data can also be used to estimate patient orientation. The patient position may be recorded and displayed at a subsequent imaging procedure so the sonographer knows how to orient the patient, as has been described previously.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of determining an anatomical scan window associated with an ultrasound image, comprising the steps of:

acquiring with an ultrasound probe a first ultrasound image with a first anatomical scan window during a first acquisition period;

analyzing the acquired first ultrasound image to determine the first anatomical scan window;

comparing a desired value of the scan window with the anatomical scan window from the analyzing step to determine whether the first anatomical scan window and the desired value of the scan window are the same or differ;

if the first anatomical scan window and the desired value of the scan window differ revert to and repeat the acquiring, analyzing, and comparing steps; and if the first anatomical scan window and the desired value of the scan window are the same,
- annotate the first ultrasound image with the determined scan window;
- store the determined scan window and the first ultrasound image in a computer memory for subsequent use, and
- retrieve the stored determined scan window and the first ultrasound image for use in a subsequent comparing step.

2. The method of claim 1, further comprising the step of displaying the first ultrasound image along with the determined scan window.